United States Patent
Kreppner et al.

(10) Patent No.: US 10,557,037 B2
(45) Date of Patent: Feb. 11, 2020

(54) COATED PIGMENTS, METHOD FOR THE PRODUCTION AND THE USE THEREOF, COATING AGENT AND ARTICLE

(71) Applicant: Eckart GmbH, Hartenstein (DE)

(72) Inventors: Simone Kreppner, Schnaittach (DE); Oliver Bedford, Ober-Ramstadt (DE); Oliver Struck, Henfenfeld (DE); Ralph Schneider, Lauf a.d. Pegnitz (DE)

(73) Assignee: ECKART GMBH, Hartenstein (DE)

( * ) Notice: Subject to any disclaimer, the term of this patent is extended or adjusted under 35 U.S.C. 154(b) by 0 days.

(21) Appl. No.: 15/546,865

(22) PCT Filed: Jan. 28, 2016

(86) PCT No.: PCT/EP2016/000143
§ 371 (c)(1),
(2) Date: Jul. 27, 2017

(87) PCT Pub. No.: WO2016/120015
PCT Pub. Date: Aug. 4, 2016

(65) Prior Publication Data
US 2018/0021240 A1 Jan. 25, 2018

(30) Foreign Application Priority Data
Jan. 28, 2015 (EP) .................................. 15152898

(51) Int. Cl.
| | | |
|---|---|---|
| *C09C 1/64* | (2006.01) |
| *C09D 7/62* | (2018.01) |
| *C09C 1/66* | (2006.01) |
| *C08K 9/08* | (2006.01) |
| *A61K 8/26* | (2006.01) |
| *A61Q 1/02* | (2006.01) |
| *A61K 8/891* | (2006.01) |
| *A61K 8/02* | (2006.01) |
| *C09D 5/03* | (2006.01) |
| *C09D 5/29* | (2006.01) |
| *C09D 7/40* | (2018.01) |
| *A61K 8/81* | (2006.01) |

(52) U.S. Cl.
CPC ............ *C09C 1/648* (2013.01); *A61K 8/0254* (2013.01); *A61K 8/26* (2013.01); *A61K 8/8152* (2013.01); *A61K 8/891* (2013.01); *A61Q 1/02* (2013.01); *C08K 9/08* (2013.01); *C09C 1/66* (2013.01); *C09D 5/035* (2013.01); *C09D 5/29* (2013.01); *C09D 7/62* (2018.01); *C09D 7/70* (2018.01); *A61K 2800/412* (2013.01); *A61K 2800/614* (2013.01); *C01P 2004/20* (2013.01); *C01P 2004/54* (2013.01); *C01P 2004/61* (2013.01); *C01P 2006/12* (2013.01); *C09C 2200/1058* (2013.01); *C09C 2200/307* (2013.01)

(58) Field of Classification Search
CPC .. C09D 7/62; C09C 1/62; C09C 1/627; C09C 1/64; C09C 1/642; C09C 1/644
See application file for complete search history.

(56) References Cited

U.S. PATENT DOCUMENTS

| | | | |
|---|---|---|---|
| 5,629,400 A | 5/1997 | Standke et al. | |
| 5,679,147 A | 10/1997 | Standke et al. | |
| 5,808,125 A | 9/1998 | Standke et al. | |
| 5,964,936 A | 10/1999 | Reisser | |
| 8,574,357 B2 | 11/2013 | Kagata et al. | |
| 9,260,584 B2 | 2/2016 | Schumacher et al. | |
| 2007/0199478 A1 | 8/2007 | Schlegl et al. | |
| 2008/0249209 A1 | 10/2008 | Trummer et al. | |
| 2009/0117281 A1* | 5/2009 | Sato .......................... C09C 1/62 427/327 |
| 2009/0131584 A1* | 5/2009 | Terao ....................... C09D 7/62 524/849 |
| 2009/0252772 A1 | 10/2009 | Henglein et al. | |
| 2010/0047199 A1 | 2/2010 | Trummer et al. | |
| 2011/0179971 A1 | 7/2011 | Proelss et al. | |
| 2014/0050768 A1 | 2/2014 | Struck et al. | |
| 2016/0304721 A1 | 10/2016 | Hippmann et al. | |

FOREIGN PATENT DOCUMENTS

| | | |
|---|---|---|
| CN | 101580653 A | 11/2009 |
| CN | 102516831 A | 6/2012 |
| DE | 102005037611 A1 | 2/2007 |
| EP | 1874874 B1 | 11/2008 |
| EP | 1613702 B1 | 10/2009 |
| EP | 2128203 A1 | 12/2009 |
| EP | 2102294 B1 | 6/2012 |
| WO | 9638505 A1 | 12/1996 |
| WO | WO 2006/041658 * | 4/2006 |
| WO | 2012130680 A1 | 10/2012 |
| WO | 2013064643 A1 | 5/2013 |
| WO | 2014048887 A1 | 4/2014 |

OTHER PUBLICATIONS

Beari et al., "Organofunctional Alkoxysilanes in Dilute Aqueous Solution: New Accounts on the Dynamic Structural Mutability", Journal of Organometallic Chemistry, 2001, pp. 208-222, vol. 625.
European Standard, "Paints and varnishes—Determination of gloss value at 20°, 60°and 85°", DIN EN ISO 2813, 2015, 30pp.

* cited by examiner

Primary Examiner — Marc S Zimmer
(74) Attorney, Agent, or Firm — The Webb Law Firm

(57) ABSTRACT

The present invention relates to a particularly effective protective coating for metallic objects, the coating method, and the special applications thereof. The particularly high protective effect is achieved by the adaptation of the inorganic fraction and the organic polymer fraction of the coating to the specific surface of the object. Further adjustments of the coating can be used for further optimization, for example of the protection properties or other product properties.

21 Claims, No Drawings

COATED PIGMENTS, METHOD FOR THE PRODUCTION AND THE USE THEREOF, COATING AGENT AND ARTICLE

CROSS-REFERENCE TO RELATED APPLICATIONS

This application is the United States national phase of International Application No. PCT/EP2016/000143 filed Jan. 28, 2016, and claims priority to European Patent Application No. 15152898.1 filed Jan. 28, 2015, the disclosures of each of which are hereby incorporated by reference in their entireties.

BACKGROUND OF THE INVENTION

Field of the Invention

The invention relates to pigments with metallic substrate and coating and also to methods for producing them and to their use. The invention further relates to coating materials comprising such pigments and to coated articles.

Description of Related Art

WO 2013/064643 A1 and WO 2014/048887 A1 relate to a two-stage coating, utilizing a combination of inorganic coating and organic coating to achieve enhanced properties. The use of an inorganic/organic hybrid layer, and especially the specific construction according to the invention, are not disclosed, however.

US 2008/0249209 A1 describes the use of inorganic/organic hybrid layers for the coating of metallic effect pigments. There is, however, no disclosure of a coating with the specific composition according to the invention, or any suggestion that enhanced properties can be achieved therewith.

The aforementioned coating variants, at least to some extent, already have very good stabilities in typical stability tests. In order to simplify the formulation of corresponding coating compositions, however, it would be advantageous to improve their stability further, in order to allow the use of new substances and to ensure a greater degree of safety in the use of new combinations of known constituents. For example, on increased addition of iron oxide, the existing metal pigments showed inadequate stability in gassing tests they were required to pass. It also proved difficult to ensure the necessary gassing stability at significantly increased pH levels. Since, however, stability is required to be extremely reliable in fields of use such as the finishing of automobiles, there is a great need to provide pigments with an even higher stability. At the same time, constituents objectionable from the standpoint of health or of ecology are to be avoided. Likewise, however, the optical properties such as the flop index of the pigments ought ideally to be retained.

SUMMARY OF THE INVENTION

In some examples, there is provided a pigment comprising a metallic substrate and at least one inorganic/organic hybrid layer, wherein the inorganic/organic hybrid layer comprises at least one metal oxide, at least one network former, and at least one organic polymer, wherein the at least one metal oxide does not constitute an oxidation product of the metallic substrate, and the term "metal oxide" comprises oxides, hydroxides, and oxide hydrates of the metals and semimetals, wherein the network former is joined at least partially covalently to the metal oxide and to the organic polymer, wherein the ratio of the amount of metal oxide of the inorganic/organic hybrid layer to the specific surface area of the uncoated metal pigment is in a range from 16.1 $mg/m^2$ to 25 $mg/m^2$, and the ratio of the amount of organic polymer of the inorganic/organic hybrid layer to the specific surface area of the uncoated metal pigment is in a range from 3.9 $mg/m^2$ to 10.1 $mg/m^2$.

In some examples, there is provided a method for producing metal pigments comprising metallic substrate and coating, comprising the following steps: i) reacting at least one metal oxide reactant, at least one reactant of an organic polymer, and at least one network former in a liquid phase to form a coating composition, ii) applying the coating composition to metallic substrates to form an inorganic/organic hybrid layer, wherein the inorganic/organic hybrid layer comprises at least one inorganic network comprising at least one metal oxide and at least one organic polymer, and the inorganic network and the organic polymer are joined covalently to one another, the at least one metal oxide does not constitute an oxidation product of the metallic substrate, and the term "metal oxide" comprises oxides, hydroxides, and oxide hydrates of the metals and semimetals, the network former is joined at least partially to the metal oxide and to the organic polymer, the ratio of the amount of metal oxide of the inorganic/organic hybrid layer to the specific surface area of the uncoated metal pigment is in a range from 16.1 $mg/m^2$ to 25 $mg/m^2$, and the ratio of the amount of organic polymer of the inorganic/organic hybrid layer to the specific surface area of the uncoated metal pigment is in a range from 3.9 $mg/m^2$ to 10.1 $mg/m^2$.

DETAILED DESCRIPTION

It is an object of the present invention, therefore, to provide pigments which exhibit improved stability. A further object of the present invention is to provide methods for producing them and also uses thereof.

Advantageously, furthermore, the optical properties of metallic effect pigments coated therewith, particularly the lightness flop of such pigments, are to be improved. Advantageously, moreover, other application-specific qualities, such as the condensation resistance, are to be at least retained. Improvements in relation to the agglomeration tendency of pigments, especially PVD pigments, would also be an advantage.

Surprisingly it has been found that, for example, the stability of pigments with metallic substrate can be increased by means of an inorganic/organic hybrid layer having a specific composition. This object for the present invention is achieved by means of a pigment comprising a metallic substrate and at least one inorganic/organic hybrid layer, the inorganic/organic hybrid layer comprising at least one metal oxide, at least one network former, and at least one organic polymer, the at least one metal oxide not constituting an oxidation product of the metallic substrate, and the term "metal oxide" embracing oxides, hydroxides, and oxide hydrates of the metals and semimetals, the network former being joined at least partially covalently to the metal oxide and to the organic polymer, the ratio of the amount of metal oxide of the coating to the specific surface area of the uncoated metal pigment being in a range from 16.1 $mg/m^2$ to 25 $mg/m^2$, and the ratio of the amount of organic polymer of the inorganic/organic hybrid layer to the specific surface area of the uncoated metal pigment being in a range from 3.9 mg/m² to 10.1 mg/m². The use of platelet-shaped metallic substrates is particularly preferred.

The aforesaid amount of metal oxide in the coating relates to the coating without any subsequent coatings applied.

An inorganic/organic hybrid layer in the sense of the present invention means that a largely homogeneous layer of the inorganic and organic constituents is present therein, without discrete successive layers being formed. As a consequence of separation processes, for example, there may, however, be inclusions or matrix-like structures of corresponding constituents formed. Hybrid layers obtained are preferably very homogeneous, having only extremely small inclusions with a size of, for example, less than 50 nm, more preferably less than 25 nm, the size of the inclusions being determined preferably by means of scanning electron microscopy. Surprisingly it has emerged that hybrid layers of this kind in the range according to the invention prove to be particularly stable.

Preferred forms of the pigments of the invention are found in claims 1 to 13 and in aspects 1 to 22.

The present invention further relates to a method for producing metal pigments comprising metallic substrate and coating, comprising the following steps:
 i) reacting at least one metal oxide reactant, at least one reactant of an organic polymer, and at least one network former in a liquid phase to form a coating composition,
 ii) applying the coating composition to metallic substrates to form an inorganic/organic hybrid layer,
the inorganic/organic hybrid layer comprising at least one inorganic network comprising at least one metal oxide and at least one organic polymer, and the inorganic network and the organic polymer being joined covalently to one another, the at least one metal oxide not constituting an oxidation product of the metallic substrate, and the term "metal oxide" embracing oxides, hydroxides, and oxide hydrates of the metals and semimetals,
the network former is joined at least partially to the metal oxide and to the organic polymer,
the ratio of the amount of metal oxide of the coating to the specific surface area of the uncoated metal pigment being in a range from 16.1 mg/m² to 25 mg/m², and
the ratio of the amount of organic polymer of the inorganic/organic hybrid layer to the specific surface area of the uncoated metal pigment being in a range from 3.9 mg/m² to 10.1 mg/m². In this context it must be understood that steps i) and ii) need not be carried out separately. Instead it is typically preferable for step i) to take place in the presence of the metallic substrate, so that the inorganic/organic hybrid layer is deposited directly on the surface of the metallic substrate.

Preferred forms of the method of the invention are found in claims 14 to 16 and in aspects 23 to 32.

The present invention further relates to the use of the pigments of the invention in a cosmetic, a plastic or a coating material.

Preferred forms of the uses of the invention are specified in claim 17 and in aspects 34 to 35.

The present invention further relates to a coating material comprising pigments of the invention.

The present invention further relates to an article which comprises the pigments of the invention or the coating materials of the invention.

The term "pigment comprising a metallic substrate" in the sense of the present invention encompasses spherical and platelet-shaped, metal-containing particles, unless otherwise specified. This includes, in particular, particles in which at least one metal layer is applied to a nonmetallic substrate, and particles consisting essentially or, preferably, completely of at least one metal or at least one metal alloy.

Unless otherwise specified, it is particularly preferred in the present invention for "substantially" to mean at least 95%, more preferably at least 99%. More particularly it is preferred for something to consist completely thereof. Where the feature in question is a physical feature, such as the amount of a specific metal or the quantity of a coating, for example, the reference is to % by weight, in the absence of any alternative specification.

The term "metallic effect pigment" in the sense of the present invention refers to platelet-shaped, metal-containing particles. The platelet-shaped metal-containing particles comprising platelet-shaped particles wherein at least one metal layer is applied to a nonmetallic platelet-shaped substrate and platelet-shaped particles consist substantially or, preferably, completely of at least one metal or at least one metal alloy. Unless otherwise specified, the terms "pigment", "metal pigment", and "metallic effect pigment" in the context of the present invention also encompass a plurality of pigments, particularly if the variable related thereto represents a statistical variable which is obtainable only in averaged form on a relatively large number of particles. In the absence of any specific details concerning such averaging, the corresponding averaged variable pertains to the arithmetic mean of the variable in question. In the sense of the present invention, the term "nonmetallic substrate" encompasses, for example, polymer substrates, glass substrates, such as glass plates, and purely metal-oxidic substrates, as for example silicon oxide platelets, aluminum oxide platelets or titanium oxide platelets. As a nonmetallic substrate it is also possible to use natural or synthetic mica platelets. More particularly, however, it is preferred for the metallic substrates of the pigments of the invention to consist substantially or, preferably, completely of metal or metal alloys.

In the case of further embodiments, it is preferred in particular if the metallic substrate is platelet-shaped.

The term "metal core" in the sense of the present invention refers to metallic substrates which consist substantially, preferably completely, of metal or metal alloys.

The term "platelet-shaped" in the sense of the present invention means that the particle in question is significantly smaller in one dimension by comparison with the remaining two dimensions. This means that, for example, the average height of the particle is at least 10 times smaller than the average width and length. The extents of the pigments are determined by methods familiar to the skilled person, an example being scanning electron microscopy. Pigments of this kind have particular advantageous properties and are at the focal point of the present invention. For example, a platelet-shaped formation permits directed reflection of electromagnetic radiation such as visible light. By this means it is possible in turn to achieve particular optical effects. A shape of maximally uniform planarity proves advantageous, for example, for achievement of particularly high brilliance, since with such shaping it is possible to achieve spatially co-directed reflection of the pigments, with only little scatter occurring.

The pigments of the invention are typically used on the basis of their optical properties. Functional effects such as changes to the heating of an article as a consequence of insolation, for example, may also be utilized, however.

Processing, sample preparation, and analysis of the pigments take place by means of methods familiar to the skilled person. Examples of such methods are HPLC (high-performance liquid chromatography), GC-MS (gas chromatography coupled with mass spectrometry), NMR (nuclear spin resonance spectroscopy, XPS (X-ray photoelectron spectroscopy), elemental analysis, or combinations of the aforementioned methods utilized with one another or with others routinely. Descriptions of corresponding possibilities for use are found for example in standard scientific works, scientific publications, and patents such as U.S. Pat. No. 8,574,357 B2. For determining the amount of metal oxide or of polymer, for example, it is essential to remove subsequent coatings or constituents, for example, of a varnish composition in which the pigments were formulated. Such residues are removed prior to measurement, for example, by washing the pigments in solvents known to the skilled person.

The specific surface area (BET surface area) is determined by commercial instruments. For the measurement it is possible, for example, to use a BELSORP-mini II from BEL Japan, Inc. A preferred measurement method is the 5-point measurement.

The term "inorganic oxide component" refers to metal oxides, with the term "metal" also encompassing semimetals, and the term "oxide" also encompassing hydroxides and oxide hydrates. More particularly it is preferred for the inorganic oxide component not to comprise an inorganic heteropoly acid. One metal oxide used with particular advantage is silicon oxide. Determining the amount of the "inorganic oxide component" is done by determining the total amount of the oxidized metal present, including in the form, for example, of hydroxides, oxide hydrates, etc., using methods familiar to the skilled person. Examples thereof are atomic absorption spectroscopy, elemental analysis, inductively coupled plasma with atomic emission spectroscopy (ICP-AES/Inductively coupled plasma atomic emission spectroscopy), and, in particular, combinations of known methods such as those stated above. The value is calculated by the amount of metal detected. Where the precise metal oxide or mixture comprising the metal oxide mixture cannot be determined by methods familiar to the skilled person such as XPS, for example, the most highly oxidized oxide of the metal that is stable under standard conditions is taken as a reference. Standard conditions in the sense of the present invention are a temperature of 0° C. and a pressure of 1.01325 bar. For silicon oxide, for example, $SiO_2$ is assumed as reference. Where the network former has corresponding constituents, in the case for example of specific organosilanes as network formers for $SiO_2$ and certain organic polymers, its individual constituents are counted as part of the metal oxide or of the organic polymer, respectively.

The term "organic polymer" refers to organic polymers and oligomers that are familiar to the skilled person. Preferably, however, this does not include any polyethylene. In the case of further embodiments, moreover, the term "organic polymer" according to the invention means preferably that the substance in question has at least 10 monomer units, more preferably at least 15 monomer units, more preferably still at least 18 monomer units.

The present invention relates to a specific coating wherein the constituents of an inorganic/organic coating layer are selected in such a way that particularly advantageous effects are achieved. In particular it proved advantageous to tailor the amount of metal oxide, based on the total amount of the coating without subsequent coatings and quantity of polymer of the inorganic/organic hybrid layer to the surface area of the object to be coated. By this means it was possible, for example, to achieve significantly greater stabilities. The metal pigments of the present invention are therefore characterized by at least one inorganic/organic hybrid layer, the ratio of the amount of metal oxide of the coating to the specific surface area of the uncoated metal pigment being in a range from 16.1 $mg/m^2$ to 25 $mg/m^2$, and the ratio of the amount of organic polymer of the inorganic/organic hybrid layer to the specific surface area of the uncoated metal pigment being in a range from 3.9 $mg/m^2$ to 10.1 $mg/m^2$.

In the case of further embodiments it is preferred, furthermore, if the ratio of the amount of metal oxide of the coating to the specific surface area of the uncoated metal pigment is at least 17.2 $mg/m^2$, more preferably at least 17.9 $mg/m^2$.

It is preferred, furthermore, in the case of further embodiments, if the ratio of the amount of metal oxide of the coating to the specific surface area of the uncoated metal pigment is at most 23 $mg/m^2$, more preferably at most 22.3 $mg/m^2$.

In the case of further embodiments it is preferred, in particular, if the ratio of the amount of metal oxide of the coating to the specific surface area of the uncoated metal pigment is in a range from 17.2 $mg/m^2$ to 23 $mg/m^2$, more preferably in a range from 17.9 $mg/m^2$ to 22.3 $mg/m^2$.

The metal oxide of the inorganic/organic hybrid layer is preferably not an oxidation product of the metal pigment. Thus the majority of metal pigments typically have a very thin superficial metal oxide layer. By a deliberate superficial oxidation, furthermore, it is possible to evoke a particular effect, usually in relation to the color; see, for example, WO 1996/038505 A1 and WO 2012/130680 A1.

It is preferred, furthermore, if the inorganic/organic hybrid layer is designed as a coating enveloping the metallic substrate.

In the case of further embodiments, furthermore, the minimum thickness of the inorganic/organic hybrid layer is preferably at least 9 nm, more preferably at least 12 nm, more preferably still at least 15 nm. Hence it has emerged that thinner inorganic/organic hybrid layers had, for example, a lower reliability in relation to the desired stability. It is thought that when too thin a coating layer is used, at least occasionally as a result of fluctuations in the production process, a completely enveloping coating layer is not achieved with certain pigments.

In the case of further embodiments, furthermore, it is preferred if the thickness of the inorganic/organic hybrid layer is at most 75 nm, more preferably at most 64 nm, more preferably still at most 52 nm. The thickness of the inorganic/organic hybrid layer is determined by methods familiar to the skilled person, such as, for example, scanning electron microscopy. In the case of relatively thick inorganic/organic hybrid layers, in particular, impairments in the optical properties have been observed. It is thought that in this case, among other factors, an increased tendency toward agglomeration is developed, thus being in part a possible explanation for the impairment of the optical effects.

In the case of further embodiments, the thickness of the inorganic/organic hybrid layer is advantageously in the range from 9 nm to 75 nm, more preferably in the range from 12 nm to 64 nm, more preferably still in the range from 15 nm to 52 nm.

In the case of further embodiments it is preferred, furthermore, if the amount of the inorganic/organic hybrid layer is at least 5 wt %, more preferably at least 6 wt %, more preferably still at least 8 wt %, based in each case on the total weight of the pigment.

In the case of further embodiments it is preferred, furthermore, if the amount of the inorganic/organic hybrid layer is at most 25 wt %, more preferably at most 21 wt %, more preferably still at most 18 wt %, based in each case on the total weight of the pigment.

In the case of further embodiments, more particularly, it is preferred if the amount of the inorganic/organic hybrid layer is in the range from 5 wt % to 25 wt %, more preferably in the range from 6 wt % to 21 wt %, more preferably still in the range from 8 wt % to 18 wt %, based in each case on the total weight of the pigment.

In the case of further variants of the present invention, furthermore, it is preferred if at least one of the network formers has a structure of formula (NI) or (NII),

  (NI)

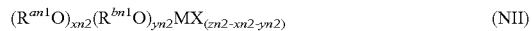  (NII)

the Xs independently of one another being selected from hydrolyzable groups after whose hydrolysis a covalent bond of organic network former to the inorganic network can be formed,
the $R^{an1}$s independently of one another being selected from reactive organic groups which can be joined covalently to the organic polymer,
the $R^{bn1}$s independently of one another being selected from organic groups which can be joined covalently to the organic polymer,
M being selected from the group consisting of Al, Zr, and Ti,
xn1 being an integer from 1 to 3, yn1 being an integer from 0 to (3−xn1),
zn2 being the formal oxidation number of M, xn2 being an integer from 1 to (zn2−1),
yn2 being an integer from 0 to (zn2−2), and
xn2+yn2≤zn2−1.

In the case of the network formers of formula (NI) and (NII), preferably the Xs independently of one another are selected from the group consisting of halogen groups, such as bromide, chloride, and iodide, the hydroxyl group, and C1-C20 alkoxy groups, which may also have heteroatoms, preferably O, S and/or N, in the carbon chain. The Xs independently of one another are preferably selected from the group consisting of halogen groups, the hydroxyl group, and C1-C4 alkoxy groups without heteroatoms in the carbon chain, more preferably from C1-C4 alkoxy groups without heteroatoms in the carbon chain. Examples of C1-C4 alkoxy groups without heteroatoms in the carbon chain are the methoxy group, ethoxy group, propoxy group, and n-butoxy group.

In the case of further embodiments, furthermore, the $R^{an1}$s are preferably selected from the group consisting of C1-C40 alkyl groups, C2-C40 alkenyl groups, C2-C40 alkynyl groups, C6-C36 aryl groups, partially fluorinated C6-C36 aryl groups, C7-C40 alkylaryl groups, C7-C40 arylalkyl groups, C8-C40 alkenylaryl groups, C8-C40 arylalkenyl groups, C8-C40 arylalkynyl groups, C8-C40 alkynylaryl groups, C5-C40 cycloalkyl groups, C6-C40 alkylcycloalkyl groups, and C6-C40 cycloalkylalkyl groups, more preferably from the group consisting of C1-C26 alkyl groups, C2-C26 alkenyl groups, C2-C26 alkynyl groups, C6-C30 aryl groups, C7-C31 alkylaryl groups, C7-C31 arylalkyl groups, C8-C32 alkenylaryl groups, C5-C20 cycloalkyl groups, C6-C21 alkylcycloalkyl groups, and C6-C21 cycloalkylalkyl groups, more preferably still from the group consisting of C1-C10 alkyl groups, C2-10 alkenyl groups, C6-C10 aryl groups, C7-C11 alkylaryl groups, and C7-C11 arylalkyl groups, it being possible for the aforementioned $R^{an1}$s to be substituted or unsubstituted. Since $R^{an1}$ represents a reactive organic group which can be joined covalently to the organic polymer, unreactive groups in the above-stated list, such as C1-C40-alkyl groups, for example, must carry functional substituents. With particular preference, $R^{an1}$ comprises substituted C1-C10 alkyl groups.

In the case of further embodiments, the substituents of $R^{an1}$ that are optionally present are preferably selected from the group consisting of amino groups, hydroxyl group, thiol groups, epoxy groups, acrylate groups, methacrylate groups, vinyl groups, allyl groups, carboxyl groups, carboxylic anhydride groups, isocyanate groups, cyanate groups, ureido groups, carbamate groups, and mixtures thereof, more preferably from the group consisting of amino groups, hydroxyl group, acrylate groups, methacrylate groups, and mixtures thereof, more preferably still from the group consisting of acrylate groups, methacrylate groups, and mixtures thereof. One example of an $R^{an1}$ group substituted accordingly is the 3-methacryloyloxypropyl group.

In the case of further embodiments, $R^{bn1}$s independently of one another are selected from the group consisting of H—, C1-C40 alkyl groups, C2-C40 alkenyl groups, C2-C40 alkynyl groups, C6-C36 aryl groups, fluorinated C6-C36 aryl groups, partially fluorinated C6-C36 aryl groups, C7-C40 alkylaryl groups, C7-C40 arylalkyl groups, C8-C40 alkenylaryl groups, C8-C40 arylalkenyl groups, C8-C40 arylalkynyl groups, C8-C40 alkynylaryl groups, C5-C40 cycloalkyl groups, C6-C40 alkylcycloalkyl groups, and C6-C40 cycloalkylalkyl groups, more preferably from the group consisting of C1-C24 alkyl groups, C2-C24 alkenyl groups, C2-C24 alkynyl groups, C6-C24 aryl groups, fluorinated C6-C24 aryl groups, partially fluorinated C6-C24 aryl groups, C7-C30 alkylaryl groups, C7-C30 arylalkyl groups, C8-C30 alkenylaryl groups, C8-C30 arylalkenyl groups, C8-C30 arylalkynyl groups, C8-C30 alkynylaryl groups, C5-C20 cycloalkyl groups, C6-C25 alkylcycloalkyl groups, more preferably still from the group consisting of C1-C24 alkyl groups, C2-C24 alkenyl groups, C6-C18 aryl groups, C7-C24 alkylaryl groups, C7-C24 arylalkyl groups, C5-C16 cycloalkyl groups, C6-C20 alkylcycloalkyl groups, the aforementioned groups being unsubstituted, and any heteroatoms present in the carbon chains and carbon ring systems being selected from the group consisting of O, N, and S. The aforesaid groups preferably contain no heteroatoms in the chain or in the ring.

In the case of further embodiments it is preferred more particularly for the network former to have a structure of formula (NI) or (NII),

  (NI)

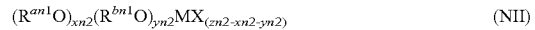  (NII)

where the Xs independently of one another are selected from the group consisting of halogen groups, the hydroxyl group, and C1-C4 alkoxy groups without heteroatoms in the carbon chain,
the $R^{an1}$s independently of one another are selected from the group consisting of C1-C26 alkyl groups, C2-C26 alkenyl groups, C2-C26 alkynyl groups, C6-C30 aryl groups, C7-C31 alkylaryl groups, C7-C31 arylalkyl groups, C8-C32 alkenylaryl groups, C5-C20 cycloalkyl groups, C6-C21 alkylcycloalkyl groups, and C6-C21 cycloalkylalkyl groups, with any substituents present being selected from the group consisting of amino groups, hydroxyl group, thiol groups, epoxy groups, acrylate groups, methacrylate groups, vinyl groups, allyl groups, carboxyl groups, carboxylic anhydride groups, isocyanate groups, cyanate groups, ureido groups, carbamate groups, and mixtures thereof, the $R^{bn1}$s independently of one another are selected from the group consisting of C1-C24 alkyl groups, C2-C24 alkenyl groups, C2-C24 alkynyl groups, C6-C24 aryl groups, fluorinated C6-C24 aryl groups, partially fluorinated C6-C24 aryl groups, C7-C30 alkylaryl groups, C7-C30 arylalkyl groups, C8-C30 alkenylaryl groups, C8-C30 arylalkenyl groups, C8-C30 arylalkynyl groups, C8-C30 alkynylaryl groups, C5-C20 cycloalkyl groups, and C6-C25 alkylcycloalkyl groups, more preferably still from the group consisting of C1-C24 alkyl groups, C2-C24 alkenyl groups, C6-C18 aryl groups, C7-C24 alkylaryl groups, C7-C24 arylalkyl groups, C5-C16 cycloalkyl groups, and C6-C20 alkylcycloalkyl groups, where the aforesaid groups are unsubstituted and any heteroatoms present in the carbon chains and carbon ring systems are selected from the group consisting of O, N, and S, M being selected from the group consisting of Al, Zr, and Ti, xn1 being an integer from 1 to 3, yn1 being an integer from 0 to (3−xn1), zn2 being the formal oxidation number of M, xn2 being an integer from 1 to (zn2−1), yn2 being an integer from 0 to (zn2−2), and xn2+yn2≤zn2−1.

It has proven particularly advantageous if the inorganic/organic hybrid layer comprises at least one network former which is selected from the group of network formers of formula (NI). It is especially preferred in this context for at least one network former to be selected from the group of the formula (NI) network formers, the Xs independently of one another being selected from the group consisting of C1-C4 alkoxy groups without heteroatoms in the carbon chain, the $R^{an1}$s independently of one another being selected from the group consisting of substituted C1-C10 alkyl groups, the substituents being selected from the group consisting of acrylate groups, methacrylate groups and mixtures thereof, the $R^{bn1}$s independently of one another being selected from the group consisting of C1-C24 alkyl groups, C6-C18 aryl groups, C7-C24 alkylaryl groups, C7-C24 arylalkyl groups, C5-C16 cycloalkyl groups, and C6-C20 alkylcycloalkyl groups, the aforesaid groups being unsubstituted and containing no heteroatoms in the carbon chains and carbon ring systems, xn1 being an integer from 1 to 3, and yn1 being 0 or 1.

Organofunctional silanes with network former suitability may be acquired from Evonik, for example. Examples are 3-methacryloyloxypropyltrimethoxysilane (Dynasylan MEMO), vinyltri(m)ethoxysilane (Dynasylan VTMO and VTEO, respectively), 3-mercaptopropyltri(m)ethoxysilane (Dynasylan MTMO or 3201), aminopropyltrimethoxysilane (Dynasylan AMMO) or 2-aminoethyl-3-aminopropyltrimethoxysilane (Dynasylan DAMO), and 3-glycidyloxypropyltrimethoxysilane (Dynasylan GLYMO). One particularly suitable group of the network formers are the 3-methacryloyloxypropyltrialkoxysilanes.

In the case of further embodiments it is preferred, furthermore, for $R^{an1}$ to have at least one functionality which corresponds to the organic polymer of the inorganic/organic hybrid layer. If the organic polymer is to be obtained, for example, through the polymerization of olefinic monomers, or if a prepolymerized organic polymer is to be bound to the network former via olefinic groups contained therein, preference is given to network formers having an olefinic group. It is especially preferred for part of the network former to be considered as part of the polymer chain of the organic polymer, so that, for example, at least one (meth)acrylate chain of the organic polymer is bound via (meth)acrylate groups to $R^{an1}$.

It has proven particularly advantageous if the network former has at least two functionalities, with at least one functionality being incorporated into the organic polymer and at least one functionality being incorporated into the inorganic network.

Further examples of organofunctional silanes having, for example, vinyl and/or (meth)acrylate functionalities are as follows: isocyanatotriethoxysilane, 3-isocyanatopropoxytriethoxysilane, vinylethyldichlorosilane, vinylmethyldichlorosilane, vinylmethyldiacetoxysilane, vinylmethyldiethoxysilane, vinyltriacetoxysilane, vinyltrichlorosilane, phenylvinyldiethoxysilane, phenylallyldiethoxysilane, phenylallyldichlorosilane, 3-methacryloyloxypropyltriethoxysilane, methacryloyloxypropyltrimethoxysilane, 3-acryloyloxypropyltrimethoxysilane, 2-methacryloyloxyethyltri(m)ethoxysilane, 2-acryloyloxyethyltri(m)ethoxysilane, 3-methacryloyloxypropyltris(methoxyethoxy)silane, 3-methacryloyloxypropyltris(butoxyethoxy)silane, 3-methacryloyloxypropyltris(propoxy)silane, 3-methacryloyloxypropyltris(butoxy)silane.

Further substances suitable as network formers are titanates, zirconates or aluminates, as are produced, for example, by Kenrich Petrochemicals and offered under the trade name Ken-React.

In the case of further embodiments of the present invention, the ratio of the amounts of substance in moles of network former to the number of monomers in the organic polymer of the inorganic/organic hybrid layer is at least 1:10, more preferably at least 1.2:10, more preferably still at least 1.4:10.

In the case of further embodiments, moreover, it is preferred if the ratio of the amounts of substance in moles of network former to the number of monomers in the organic polymer of the inorganic/organic hybrid layer is at most 5:10, more preferably at most 4:10, more preferably still at most 3.5:10.

In the case of further embodiments of the present invention, it is especially preferred if the ratio of the amounts of substance in moles of network former to the number of monomers in the organic polymer of the inorganic/organic hybrid layer is in the range from 1:10 to 5:10, more preferably in the range from 1.2:10 to 4:10, more preferably still in the range from 1.4:10 to 3.5:10.

Further variants of the present invention are further characterized in that the organic polymer preferably consists substantially of monomers which have at least one functionality or had one such functionality prior to the polymerization, said functionalities being selected from the group consisting of amino groups, thiol groups, epoxy groups, acrylate groups, methacrylate groups, vinyl groups, allyl groups, alkenyl groups, alkynyl groups, carboxyl groups, carboxylic anhydride groups, isocyanate groups, cyanate groups, ureido groups, and carbamate groups, more preferably from the group consisting of acrylate groups, methacrylate groups, hydroxyl groups, carboxyl groups, and carboxylic anhydride groups, more preferably still from the group consisting of acrylate groups and methacrylate groups. The organic polymer consists preferably to an extent of at least 99 wt %, more preferably completely, of such monomers. In particular it is preferred for the aforesaid reactive groups to have undergone substantially complete reaction during the polymerization.

In the case of further embodiments, the organic polymer is preferably selected from the group consisting of polyacrylates, polymethacrylates, polyethers, polyesters, polyamines, polyamides, polyols, polyurethanes, and polyolefins, the polyolefins including no polyethylene, more preferably from the group consisting of polyacrylates, polymethacrylates, polyethers, and polyesters, more preferably still from the group consisting of polyacrylates and polymethacrylates.

The organic polymer is preferably bonded covalently via the functional group $R^{an1}$ of one or more organic network formers in the inorganic/organic hybrid layer.

In the case of further embodiments it is preferred if the ratio of the amount of organic polymer of the inorganic/organic hybrid layer to the specific surface area of the uncoated metal pigment is at least 4.6 mg/m$^2$, more preferably at least 5.1 mg/m$^2$.

In the case of further embodiments it is preferred, moreover, if the ratio of the amount of organic polymer of the inorganic/organic hybrid layer to the specific surface area of the uncoated metal pigment is at most 9.7 mg/m$^2$, more preferably at most 9.5 mg/m$^2$.

In the case of further embodiments, it is especially preferred if the ratio of the amount of organic polymer of the inorganic/organic hybrid layer to the specific surface area of the uncoated metal pigment is in a range from 4.6 mg/m$^2$ to 9.7 mg/m$^2$, more preferably in a range from 5.1 mg/m$^2$ to 9.5 mg/m$^2$.

It has emerged, furthermore, that preferably a certain weight ratio of the amount of metal oxide in the coating to the amount of organic polymer in the inorganic/organic hybrid layer is present. In the case of further embodiments, the weight ratio of the amount of metal oxide in the coating to the amount of organic polymer in the inorganic/organic hybrid layer is at least 2.5:1, more preferably at least 3.0:1, more preferably still at least 3.3:1.

In the case of further embodiments, furthermore, it is preferred if the weight ratio of the amount of metal oxide in the coating to the amount of organic polymer in the inorganic/organic hybrid layer is at most 9.0:1, more preferably at most 8.1:1, more preferably still at most 6.7:1.

In the case of further embodiments, it is especially preferred if the weight ratio of the amount of metal oxide in the coating to the amount of organic polymer in the inorganic/organic hybrid layer is in a range from 2.5:1 to 9.0:1, more preferably in a range from 3.0:1 to 8.1:1, more preferably still in a range from 3.3:1 to 6.7:1.

According to further variants of the present invention, it is preferred if the metal oxides of the inorganic/organic hybrid layer are selected substantially, more preferably completely, from the group consisting of silicon oxide, aluminum oxide, boron oxide, zirconium oxide, cerium oxide, iron oxide, titanium oxide, chromium oxide, tin oxide, molybdenum oxide, vanadium oxide, zinc oxide, magnesium oxide, and mixtures thereof, more preferably from the group consisting of silicon oxide, aluminum oxide, iron oxide, and mixtures thereof, the aforementioned metal oxides also including their hydroxides and oxide hydrates. With particular preference the metal oxides for application in accordance with the invention are selected substantially, preferably completely, from the group consisting of silicon oxide, aluminum oxide, and mixtures thereof, the aforementioned metal oxides also including their oxide hydrates and hydroxides. Having proven advantageous in particular is the use of silicon oxides such as silicon dioxide, silicon hydroxide, silicon oxide hydrate, and mixtures thereof. In the case of further embodiments it is preferred, furthermore, if at least 90 wt %, more preferably at least 97 wt %, of the metal oxides of the inorganic/organic hybrid layer are selected from the aforementioned metal oxides.

The term "metal oxide layer" or "metal oxide" in the sense of the present invention also comprises, unless the contrary is specified, oxidized forms of the metals and semimetals such as hydroxides and oxide hydrates.

Typically it has proven advantageous if the amount of metal oxide in the coating is at least 50 wt %, preferably at least 56 wt %, more preferably still at least 61 wt %, based in each case on the total weight of the coating In the case of further embodiments, furthermore, it is preferred if the amount of metal oxide in the coating is at most 86 wt %, preferably at most 82 wt %, more preferably still at most 79 wt %, based in each case on the total weight of the coating.

In the case of further embodiments it is especially preferred if the amount of metal oxide in the coating is in a range from 50 wt % to 86 wt %, preferably in a range from 56 wt % to 82 wt %, more preferably still in a range from 61 wt % to 79 wt %, based in each case on the total weight of the coating.

In the case of further embodiments it is preferred, furthermore, if the specified constituents of the inorganic/organic hybrid layer, in other words the at least one metal oxide, the at least one organic polymer, and the at least one network former, constitute at least 80 wt %, more preferably at least 90 wt %, more preferably still at least 97 wt %, of the inorganic/organic hybrid layer, based on the total weight of the inorganic/organic hybrid layer.

In the case of further embodiments it is preferred, furthermore, if the total amount both of the at least one metal oxide and also the total amount of the at least one organic polymer in the inorganic/organic hybrid layer is in each case at least 10 wt %, more preferably at least 20 wt %, based in each case on the total weight of the inorganic/organic hybrid layer. Hence it was found, with inadequate amounts of metal oxide or organic polymer, that the advantageous properties of the inorganic/organic hybrid layer were much less strongly pronounced.

It was found, furthermore, that inadequate amounts of network former result in a marked deterioration in the protective effect of the inorganic/organic hybrid layer. In the case of further embodiments, the total amount of the network formers in the inorganic/organic hybrid layer is preferably at least 1.5 wt %, more preferably at least 1.8 wt %, more preferably still at most 2.3 wt %, based in each case on the total weight of the inorganic/organic hybrid layer.

It emerged, furthermore, that excessive amounts of network former either no longer provided any improvement or may even result in a deterioration in the optical properties. In the case of further embodiments, the total amount of the network formers in the inorganic/organic hybrid layer is preferably at most 9.2 wt %, more preferably at most 8.5 wt %, more preferably still at most 7.9 wt %, based in each case on the total weight of the inorganic/organic hybrid layer.

In the case of further embodiments it is especially preferred if the total amount of the network formers in the inorganic/organic hybrid layer is in the range from 1.5 wt % to 9.2 wt %, more preferably in the range from 1.8 wt % to 8.5 wt %, more preferably still in the range from 2.3 wt % to 7.9 wt %, based in each case on the total weight of the inorganic/organic hybrid layer.

In further variants of the present invention, the pigments of the invention may furthermore comprise further coating layers as well as the inorganic/organic hybrid layer. This allows the product properties to be adapted further. By this means it is possible to exert further influence over the properties. In order to simplify the production process, on the other hand, it is preferred in further embodiments if the coating of the invention comprises only the inorganic/organic hybrid layer and also, optionally, substantially pure metal oxide coatings and subsequent coatings. Subsequent coating is carried out using preferably monomeric and polymeric silanes, especially preferably precondensed heteropolysiloxanes. Examples of silanes which can be used as a subsequent coating are Dynasylan 9116, Dynasylan OCTEO, Dynasylan AMMO, and Dynasylan DAMO.

In the case of further embodiments, there is at least one discrete coating layer disposed on the inorganic/organic hybrid layer and constituting a substantially purely inorganic layer or consisting substantially of organic polymer.

For the further modification of the pigments it is possible, for example, for further coating layers to be applied, consisting substantially of metal oxide. For the purposes of this invention, the term "substantially consisting of metal oxide" or, for example, "substantially consisting of silicon oxide, silicon hydroxide, silicon oxide hydrate or mixtures thereof" is understood to mean that the layer consists predominantly, preferably to an extent of at least 90 wt %, more preferably at least 95 wt %, more preferably still at least 99 wt %, of metal oxide or, respectively, of silicon oxide, silicon hydroxide, silicon oxide hydrate or mixtures thereof. For example, layers in question which have been produced by means of the sol-gel process and not calcined may also contain alkoxy groups. The at least one coating layer to be applied in accordance with the invention and comprising at least one metal oxide preferably comprises (an) uncalcined coating(s). "Uncalcined" in the sense of the present invention means that no heating has taken place to bring about substantially complete removal of the water present in the layer applied by sol-gel processes. This may be done, for example, by heating above 400° C. By this means, for example, pigments can be obtained whose "water content" in the layer in question is less than 3 wt %.

In the case of further embodiments, the pigment of the invention has at least one coating layer which consists substantially of metal oxide, the metal oxide being preferably selected from the group consisting of silicon oxide, titanium oxide, aluminum oxide, zirconium oxide, iron oxide, copper oxide, tin oxide, cobalt oxide, chromium oxide, cerium oxide, zinc oxide, antimony oxide, manganese oxide, nickel oxide, yttrium oxide, molybdenum oxide, vanadium oxide, tantalum oxide, tungsten oxide, and mixtures thereof, more preferably from the group consisting of silicon oxide, titanium oxide, aluminum oxide, iron oxide, copper oxide, cerium oxide, and mixtures thereof, with the aforementioned metal oxides also encompassing hydroxides and oxide hydrates. The aforementioned at least one coating layer consisting substantially of metal oxide is preferably not an oxidation product of the metallic substrate.

In the case of pigments where the optical effect is not to be influenced by interference effects because of the coating, the use of low-index metal oxides has proven advantageous. This concerns preferably the metal oxide-containing coating layers which are different from the inorganic/organic hybrid layer. The term "low-index" in the sense of the present invention means that their refractive index is at most 1.7. This figure relates to the refractive index of the relevant metal oxide in macroscopic form. This index may be determined by means of commonplace methods, as for example by means of a refractometer. In the case of further embodiments, therefore, the metal oxides of the coating are selected to an extent of at least 95 wt %, preferably at least 99 wt %, from the group of low-index metal oxides, based in each case on the total weight of the coating. In the case of further embodiments it is preferred if less than 10 wt %, more preferably less than 3 wt %, more preferably still less than 1 wt % of the metal oxides present in the coating are not low-index metal oxides, based on the total weight of the metal oxides of the coating. A particularly preferred low-index metal oxide is silicon oxide, comprising more particularly silicon dioxide, silicon hydroxide, silicon oxide hydrate, and mixtures thereof.

In the case of further embodiments it is preferred, furthermore, for all coating layers which are different from the inorganic/organic hybrid layer, which consist substantially of metal oxide, and which have not been formed from oxidation of the metal of the metallic substrate and/or of the metal core, consist substantially of silicon oxide, silicon hydroxide, silicon oxide hydrate or mixtures thereof.

In the case of further embodiments, furthermore, it is preferred if the pigment of the invention comprises at least one coating layer consisting substantially of organic polymer, the polymer of this coating layer being preferably selected substantially or completely from the group consisting of poly(meth)acrylate, polyether, polyester, polyamine, polyamide, polyol, polyurethane, polyphenol-formaldehyde, polyolefin, and mixtures thereof. In the case of further embodiments, the polymers of all coating layers consisting substantially of organic polymer are selected from the aforesaid polymers.

In the case of further embodiments it is particularly preferred if the pigment of the invention comprises at least one coating layer consisting substantially of organic polymer, the polymer being a poly(meth)acrylate. The term "poly(meth)acrylate" or "(meth)acrylate" in the sense of the present invention means that the constituent in question comprises acrylates, methacrylates or mixtures thereof.

According to a further variant of the present invention, specific metallic substrates are utilized. Thus, for example, it has been found that by combining the coatings of the invention with specific metallic substrates, it is possible to obtain particularly advantageous properties for common applications in relation in particular to the optical properties or the protection properties.

In the case of further embodiments it is preferred if the pigments of the invention, more particularly the metallic effect pigments, have an average pigment diameter ($D_{50}$) in a range from 2 to 66 μm, preferably in a range from 4 to 50 μm, more preferably still in a range from 8 to 47 μm.

The D value is a parameter familiar to the skilled person for the characterization of metallic substrates of this kind. The number respectively reported in this case indicates what % of the particles in a volume-averaged particle size distribution lie below a specified size. For example, the $D_{50}$ indicates the size below which 50% of the particles lie. The measurements are made, for example, by laser granulometry, using a particle size analyzer from Quantachrome (instrument: Cilas 1064). The measurement here is made according to manufacturer details. For this purpose, 1.5 g of the pulverulent coating material or paste with a solids content of 1.5 g are dispersed in about 100 ml of ethanol, treated in an ultrasound bath (instrument: Sonorex IK 52, from Bandelin) for 300 seconds, and then transferred using a Pasteur pipette into the sample preparation cell of the instrument, and subjected to repeated measurement. The resulting averages are formed from the individual results. Scattered light signals here are analyzed in accordance with the Fraunhofer method.

Furthermore, the $D_{90}$ lies preferably in a range from 10 to 81 μm, more preferably in a range from 16 to 80 μm, and more preferably still in a range from 21 to 79 μm.

It is more preferred, moreover, if the $D_{10}$ lies in a range from 0.5 μm to 34 μm, more preferably in a range from 1 μm to 29 μm, and more preferably still in a range from 2 μm to 27 μm.

In embodiments of the invention it is especially preferred if the $D_{50}$ lies in a range from 2 μm to 66 μm, the $D_{90}$ in a range from 10 μm to 81 μm, and the $D_{10}$ in a range from 0.5 μm to 34 μm. With preference, the $D_{50}$ lies in a range from 4 μm to 50 μm, the $D_{90}$ in a range from 16 μm to 80 μm, and the $D_{10}$ in a range from 1 μm to 29 μm.

A further feature for characterizing the pigments of the invention, preferably metallic effect pigments, is the span ΔD, which is defined as follows:

$$\Delta D = (D_{90} - D_{10})/D_{50}.$$

The pigments of the invention, more particularly the metallic effect pigments, preferably have a span in a range from 0.6 to 2.1, preferably in a range from 0.7 to 1.9, and more preferably still in a range from 0.75 to 1.7.

Furthermore, the coated metallic effect pigments, preferably metallic effect pigments, of the invention are notable preferably for a defined average thickness ($h_{50}$). The average thickness indicates the value designating 50% of the metal pigments in a cumulative frequency distribution that have the specified thickness or less, with measurement being carried out on at least 100 pigments—for example, 100 pigments.

The preparation and the measurement of the pigments for the determination of the thickness distribution take place in accordance with the method described in US 2007/0199478 A1 ([0129-[0131]). Here, only pigments with an azimuthal angle of below 10° are counted. The determination of relevant indices of the cumulative frequency distribution may take place, for example, by means of a standard program such as Excel (quantile function).

Should the aforementioned method not be applicable for the preparation of the pigments, preparation in varnish may be done as an alternative for example. In this case, the best possible orientation of the platelets within the application medium is important. The cured varnish is subsequently sectioned and the ground section is viewed in SEM. For the count, only particles having a good orientation are selected.

In the case of the coated metallic effect pigments of the invention, then, it is preferred if the $h_{50}$ lies in a range from 15 nm to 2 μm, preferably in a range from 20 nm to 1.5 μm. In the case of further embodiments it is especially preferred if the coated metallic effect pigments of the invention have an $h_{50}$ in a range from 20 nm to 370 nm, more preferably in a range from 20 nm to 240 nm, and very preferably in a range from 15 to 80 nm, and especially preferably in a range from 20 to 50 nm.

To characterize the metallic effect pigments particularly preferred in accordance with the invention it is possible, for example, to employ the aspect ratio. This ratio is given by the following formula:

$$\text{aspect ratio} = \frac{D_{50}}{h_{50}}.$$

Thus the coated metallic effect pigments of the invention in the case of preferred embodiments are characterized by an aspect ratio in a range from 1500:1 to 10:1, preferably in a range from 1200:1 to 15:1, more preferably in a range from 950:1 to 25:1.

The term "metallic substrates" in the sense of the present invention refers to uncoated, metal-containing pigments which have no more than a thin oxidation layer. The metallic substrates advantageously are metallic effect pigments. These are preferably metal pigments which consist substantially, preferably completely, of at least one metal or at least one metal alloys. In particular, the metallic substrates are not nanoparticles or agglomerates of nanoparticles. The term "nanoparticle" in the sense of the present invention refers to particles having an average particle size of less than 400 nm. The metallic substrates preferably do not comprise particles having an average particle size of less than 500 nm or agglomerates thereof. Particles with these small sizes are determined for example by means of a DelsaNano C instrument from Beckman Coulter in accordance with manufacturer details.

In the case of applications where high metallic gloss values are desired without serious changes in color through oxidation of the metallic substrate, it is preferred if the metal of the metallic substrate of the invention that is used is present largely in elemental metal form, and thus in non-oxidized form. In the case of further embodiments, therefore, the oxygen content of the metal of the metallic substrate is at most 15 wt %, preferably at most 12 wt %, more preferably at most 8 wt %, more preferably still at most 5 wt %, and most preferably at most 3 wt %, based in each case on the weight of the metal of the metallic substrate.

Where, however, specific shades are desired, they can be achieved without additional color pigments, or in addition to color pigments that are present, by means of coloring through deliberate oxidation of the metal pigments to generate a color-imparting oxide layer.

In the case of further embodiments it is preferred if the metal of the metallic substrate consists largely of a metal selected from the group consisting of aluminum, copper, iron, zinc, tin, titanium, stainless steel, mixtures thereof, and alloys thereof, more preferably from the group consisting of aluminum, iron, copper, and brass. Consisting "largely" of a metal X or of a mixture of the metals X to Z in the sense of the present invention means that the metal X or the mixture of the metals X to Z constitutes at least 60 wt %, based on the weight of the metal of the metallic substrate without oxygen, or the metal core without oxygen. The metal of the metallic substrate or of the metal core consists preferably to an extent of at least 95 wt %, more preferably to an extent of at least 99 wt %, of the specified metal or specified metals, based in each case on the weight of the metal of the metallic substrate without oxygen or of the metal core without oxygen.

In the case of further embodiments it is especially preferred if the metallic substrate comprises a metal core. This metal core consists preferably largely of a metal selected from the group consisting of aluminum, copper, iron, zinc, tin, titanium, chromium, cobalt, silver, stainless steel, nickel, antimony, magnesium, zirconium, silicon, and boron, and mixtures and also alloys thereof. In the sense of the present invention, the term "metal" also encompasses the semimetals silicon and boron, more particularly silicon, which are employed preferably as an alloy constituent. The aforesaid metals preferably represent at least 95 wt % of the metal core, based on the weight of the metal core without oxygen. Owing to superficial oxidation, which in the majority of cases is hard to avoid, the oxygen content is not taken into account when calculating the proportions of the aforesaid metals.

In the case of further embodiments it is preferred if the above-stated and also subsequent details of the present invention relate not to the metal of the metallic substrate and to the weight of the metal of the metallic substrate, but instead to the metal core and to the weight of the metal core.

In the case of further embodiments it is preferred if the metal of the metallic substrate consists to an extent of at least 95 wt % of a metal selected from the group consisting of aluminum, iron, zinc, tin, silver, copper, chromium, titanium, and mixtures thereof, based on the weight of the metal of the metallic substrate without oxygen.

Preferred mixtures of the metals are brass (gold bronze), zinc-magnesium alloys, and steel.

Particularly preferred are metal cores consisting to an extent of at least 95 wt % of aluminum, iron, zinc, steel, copper or brass, more preferably aluminum, copper, iron or brass, based on the weight of the metal core without oxygen.

One particularly preferred group of metallic substrates are nonmetallic substrates coated with aluminum, and metal cores selected from aluminum pigments. Especially preferred are metal cores selected from aluminum pigments. In the case of further embodiments, the metal of the metallic substrate consists preferably to an extent of at least 95 wt % of aluminum, based on the weight of the metal of the metallic substrate without oxygen. In the case of further embodiments, furthermore, it is preferred if the fraction of other metals in the metallic substrates is less than 1 wt %, more preferably less than 0.1 wt %, based on the weight of the metal of the metallic substrate without oxygen.

Another preferred group of metallic substrates are copper-containing metallic substrates. They have an elemental copper content of at least 50 wt %, more preferably of at least 70 wt %, based in each case on the weight of the metal of the metallic substrate without oxygen. It is especially preferred if copper-containing metal cores are used. In the sense of the invention, the aforementioned elemental copper content also comprehends the copper fraction present in an alloy. Particularly preferred is the use of platelet-shaped, copper-containing pigments, also called copper effect pigments below.

According to further embodiments, copper pigments, more particularly copper effect pigments, are employed as metallic substrates. "Copper pigments" in the sense of the present invention preferably have an elemental copper content of 98 to 100 wt %, more preferably of 99 to 99.999 wt %, based in each case on the weight of the metal of the metallic substrates. In the case of further embodiments it is especially preferred if the copper pigments are metal cores. It should be understood that when 100 wt % of copper is stated, the skilled person also reads in customary extraneous metals present possibly in trace amounts. The term "trace amount" in the sense of the present invention refers to amounts of preferably at most 0.01 wt %, based on the total weight of the metal.

According to further embodiments, in the present invention, brass pigments, more particularly platelet-shaped brass pigments, also called brass effect pigments below, are employed as metallic substrates. The term "brass pigment" in the sense of the present invention refers to metallic pigments wherein the metal is selected from an alloy consisting at least largely of zinc and copper. Pigments of this kind are also referred to as gold bronze pigments. The brass pigments employed in accordance with the invention, more particularly brass effect pigments, preferably have a copper content of 70 to less than 98 wt %, more preferably of 75 to 90 wt %, based in each case on the weight of the metal of the metallic substrate without oxygen. In the case of further embodiments it is especially preferred if the brass pigments are metal cores.

Zinc, alongside copper, forms another major constituent of the metal of the brass pigments, with the total amount of copper and zinc in the case of further embodiments being preferably at least 95 wt %, more preferably at least 99 wt %, more preferably still at least 99.9 wt %, based in each case on the weight of the metal of the copper-containing metallic substrate without oxygen.

Generally speaking, platelet-shaped metal pigments, especially those explicitly set out above, can be obtained by means of various processes familiar to the skilled person. Examples of such processes are the milling of atomized metal powder, more particularly atomized aluminum powder, atomized copper-containing powder, and atomized iron powder, or the vapor deposition of metal, more particularly of aluminum, in a PVD process. The two aforesaid production processes differ not solely in the pigment quality that is typically achieved or achievable, but also in the requirements relating to further processing, in their handling, and in their specific properties.

One widespread method for obtaining a broad spectrum of metallic effect pigments having very different properties is the milling of atomized metal powder. In this process, typically liquid metal is atomized to obtain a fine metal powder. In the metal melt there may also be different metals alloyed with one another. An example is the production of atomized brass powder. The atomized powder obtained is subsequently subjected to optional classifying or after treatment before being milled.

Milling may take place wet or dry. The corresponding process variant is selected on the basis, among others, of the desired framework conditions, the desired products, and the reactants employed. Thus, for example, wet milling proved to have advantages from a safety standpoint, and resulted in more uniform and gentler deformation even in the case of fewer optimized process parameters. In the milling of aluminum, for example, wet milling is typically preferred. Dry milling, on the other hand, offers simplified processing, since there is no need, for example, for subsequent rewetting to a different solvent. It finds application, for example, in the milling of atomized copper powder or brass powder to form platelet-shaped copper or brass pigments, respectively. The term "wet milling" describes the milling of the pigments in the presence of a solvent.

In the case of milling, the atomized metal powder is milled in ball mills in a plurality of milling stages under different milling conditions, such as mill size, mill diameter, mill rotary speed, ball size, milling time with addition of lubricant, such as stearic acid or oleic acid, to prevent cold welding of the metal particles, with milling taking place using grinding media, such as steel balls, for example. After milling and optional classifying, the platelet-shaped metal pigments are collected in various containers and subsequently homogenized or mixed.

Further information on a milling process which can be employed in this context is given in US 2011/0179971 A1, the disclosure content of which is hereby referenced in its entirety.

The aforementioned metallic effect pigments produced by milling may be produced for example in accordance with the process described in US 2007/0199478 A1 or US 2010/0047199 A1.

According to one further embodiment, therefore, pigments obtained by grinding and having an $h_{50}$ in the range from 20 to 100 nm, a form factor of at least 200, and a relative thickness distribution $\Delta h$ in the range from 30 to 140% are used as metal cores. The $\Delta h$ value is calculated according to formula VII:

$$\Delta h = (h_{90} - h_{10})/h_{50} \quad \text{(VII)}$$

Metal pigments of these kinds are produced as described in EP 1 613 702 B1, EP 2 102 294 B1, and EP 2 128 203 A1.

PVD metallic effect pigments have an absolute planar surface and outstanding optical properties. In particular, the construction of pigments produced by physical vapor deposition is virtually ideal for optical effects. The resulting outstanding optical properties make these pigments of particular advantage for very high-quality applications.

A problem of the aforesaid pigments, especially of the PVD pigments, to date was their severe agglomeration tendency, which made concentration difficult and drying impossible without significantly impairing the advantageous properties, especially the optical properties.

Using pigments obtained by milling and having an $h_{50}$ in the range from 20 to 100 nm, a form factor of at least 200, and a $\Delta h$ in the range from 30 to 140%, or using PVD pigments as metallic substrates for the metallic effect pigments of the invention, pigments of high brilliance for use in paints, printing inks, varnishes, and cosmetics are obtained. In the case both of pigments obtained by milling and of PVD pigments, preference is given particularly to aluminum, copper, brass (gold bronze), and iron pigments, preferably aluminum pigments.

In the case of further embodiments it is preferred if not only the pigments obtained by PVD processes but also the pigments obtained by milling have an $h_{50}$ in the range from 20 to 100 nm, a form factor of at least 200, and a $\Delta h$ in the range from 20 to below 70%, preferably from 25 to 65%, more preferably from 30 to 60%. Preferably the $h_{50}$ is in the range from 23 to 50 nm, the form factor at least 250, and the $\Delta h$ in the range from 20 to below 70%, preferably from 25 to 65%, more preferably from 30 to 60%. The production of aluminum pigments of this kind by wet milling is described for example in US 2010/047199 (A1).

For example, the use of polymer foils or else the high quantities of energy required to vaporize the metals make it very costly to produce PVD pigments. If pigments of particularly high quality and outstanding brilliance are required, preference is given in the case of further embodiments to the metal pigments produced by PVD processes. If, on the other hand, very high-quality pigments with outstanding brilliance and low costs are required, preference is given to the metal pigments produced by milling.

Surprisingly it has emerged, furthermore, that through the application of a precondensed heteropolysiloxane to a metal oxide-containing coating layer, as for example the inorganic/organic hybrid layer of the invention, it is possible to utilize significantly higher concentrations of pigment suspensions without marked agglomerations occurring. A particular surprise was that a powder was obtainable without addition of binders even from PVD pigments with a particular agglomeration tendency and from particularly high-quality pigments obtained by milling, with an additional coating of precondensed heteropolysiloxanes.

In the case of further embodiments, a precondensed heteropolysiloxane was applied to at least one inorganic/organic hybrid layer, the at least one precondensed heteropolysiloxane comprising at least one aminosilane and at least one silane selected from the group consisting of alkylsilanes, vinylsilanes, and arylsilanes, and the heteropolysiloxane having been applied in precondensed form.

The possibility of being able to process high-quality yet sensitive pigments, such as PVD pigments in particular, in highly concentrated form without risk of substantial quality detractions results in a number of advantages. For example, the handling of the pigments is made easier, and the application possibilities are greatly expanded. In addition, the purification of the pigments is made more simple, and a consistently high quality at the premises of the end user is ensured, with reduced transport, storage, and processing requirements.

The possibility of a significant concentration of PVD pigments and even of their drying permits an entirely new handling of the pigments. For example, such pigments can be isolated by filtration by means of simple method steps, without marked losses in quality, ahead of further processing steps. For example, following complete removal of the solvent, the pigments can be used directly in solvent-free coating applications. For example, the transport and the storage are very greatly simplified by means of the possibility for removal of the solvent. For example, new modification options, as for example a modification of the pigments in a gas-phase reaction, are provided. For example, the present invention allows the pigments to be used in solvent-free systems, such as powder coating material or plastics, or in systems where solvents may cause problems, such as UV varnishes and printing inks. For example, constituents which in the product would tend toward migration can easily be removed. This simplifies, or indeed makes possible, the use of pigments in the food sector. For example, rewetting to a different solvent, in other words a replacement of the solvent, is made significantly easier.

The precondensed heteropolysiloxanes preferably have an average molecular weight of at least 500 g/mol, more preferably of at least 750 g/mol, and very preferably of at least 1000 g/mol. The average molecular weight may be effected for example by means of NMR spectroscopy methods such as $^{29}$Si NMR, optionally in conjunction with $^1$H NMR. A description of such methods is found for example in publications such as "Organofunctional alkoxysilanes in dilute aqueous solution: new accounts on the dynamic structural mutability", Journal of Organometallic Chemistry 625 (2001) 208-216.

Furthermore, surprisingly, in the case of the pigments of the invention, good applicability, very good hiding and abrasion resistance were found when used in a powder coating material. In particular, the coating for application in accordance with the invention proved advantageous in the coating of ferromagnetic pigments, which, moreover, could be aligned particularly effectively during or after application of the powder coating material.

In the case of further embodiments, it is preferred if the pigments of the invention have a coating layer which is produced by application of a precondensed heteropolysiloxane. With more particular preference the precondensed heteropolysiloxane is applied to a metal oxide-containing coating layer, preferably the inorganic/organic hybrid layer of the invention.

The precondensed heteropolysiloxane can be applied in a variety of ways. Having proven particularly advantageous is the addition of the polysiloxane, preferably in dissolved or dispersed form, to a suspension comprising the metal pigments to be coated. In this case, a reaction product obtained from a preceding coating step can be used, for example, for the provision of the suspension comprising the metal pigments to be coated.

The structure of the precondensed heteropolysiloxanes may in particular be catenated, cyclic, crosslinked, or mixtures thereof.

In the case of further embodiments it is preferred, furthermore, if the precondensed heteropolysiloxane is composed at least to an extent of 87 wt %, preferably at least to an extent of 93 wt %, more preferably at least to an extent of 97 wt %, based on the total weight of the precondensed heteropolysiloxane, of silane monomer components selected from the group consisting of aminosilanes, alkylsilanes, vinylsilanes, arylsilanes, and mixtures thereof. With more particular preference the precondensed heteropolysiloxane is composed of the aminosilane components and alkylsilane components in the aforesaid quantities.

The silane monomers are used for example in the form of alkoxides. For the polymerization, this alkoxide bond is cleaved, and, in a condensation step, the silane monomers are crosslinked or reacted to give the respective precondensed heteropolysiloxane. The alkoxides used for the present invention are preferably methoxides and ethoxides. Unless otherwise specified, the wt % of the silane monomer components in the precondensed heteropolysiloxane in the sense of the present invention is based on the weight of the silane monomers without the constituents which are eliminated subsequent to the condensation to form the precondensed heteropolysiloxane, such as alkoxy groups, for example. The preparation of polysiloxanes of this kind is described in the literature. Corresponding preparation processes are found for example in U.S. Pat. Nos. 5,808,125 A, 5,679,147 A, and 5,629,400 A.

Having proven to be particularly advantageous aminosilanes which can be used for constructing the precondensed heteropolysiloxanes useful in accordance with the invention are aminosilanes having 1 or 2 amino groups per Si atom. In the case of further embodiments, the aminosilane components present in the precondensed heteropolysiloxane are selected to an extent of at least 92 wt %, preferably at least 97 wt %, from aminosilanes having 1 or 2 amino groups, based in each case on the total weight of the aminosilane components present in the precondensed heteropolysiloxane.

Having proven advantageous, for example, are ($H_2N(CH_2)_3)Si(OCH_3)_3$ ((3-aminopropyl)(trimethoxy)silane, AMMO), $H_2N(CH_2)_3Si(OC_2H_5)_3$ ((3-aminopropyl)(triethoxy)silane, AMEO), $(H_2N(CH_2)_2)NH(CH_2)_3)Si(OCH_3)_3$ ((N-(2-aminoethyl)-3-aminopropyl)(trimethoxy)silane, (DAMO)), $(H_2N(CH_2)_2NH(CH_2)_3)Si(OC_2H_5)_3$ (N-(2-aminoethyl)-3-aminopropyl)(triethoxy)silane), and mixtures thereof. In the case of further embodiments, the aminosilane components present in the precondensed heteropolysiloxane are selected to an extent of at least 92 wt %, preferably at least 97 wt %, of the aforementioned groups and mixtures thereof, based in each case on the total weight of the aminosilane components present in the precondensed heteropolysiloxane.

In the case of further embodiments it is preferred if the precondensed heteropolysiloxane used in accordance with the invention contains only small amounts, or none at all, of epoxysilanes. Thus pigments comprising corresponding precondensed heteropolysiloxanes typically exhibited better adhesion in common wet coating systems. In the case of further embodiments it is especially preferred if the precondensed heteropolysiloxane comprises at most 10 wt %, preferably at most 6 wt %, more preferably at most 4 wt %, and more preferably still at most trace amounts of epoxysilane components, based in each case on the total weight of the precondensed heteropolysiloxane.

It has emerged, furthermore, that even small amounts of precondensed heteropolysiloxane are typically sufficient. In the case of further embodiments, the coating layer comprising the at least one, preferably one, precondensed heteropolysiloxane has an average thickness of at most 20 nm, more preferably at most 10 nm. It is especially preferred here if the at least one, preferably one, precondensed heteropolysiloxane is present substantially as a monolayer.

It has proven particularly advantageous if at least one precondensed heteropolysiloxane has been applied to an enveloping coating layer comprising silicon oxide.

The precondensed heteropolysiloxanes used in accordance with the invention can be prepared by condensing, for example, alkylsilanes and aminosilanes. The skilled person, however, is aware that identical precondensed heteropolysiloxanes can also be prepared by another route, as for example by reaction of at least one alkylsilane, at least one haloalkylsilane, and at least one amine. Precondensed heteropolysiloxanes of this kind, which could also be seen formally as condensation products of corresponding alkylsilanes and aminosilanes, are presently embraced in accordance with the invention. In knowledge of the present invention and with an eye to the known art knowledge, the skilled person is able to select from a variety of retrosynthetic routes.

In the case of further embodiments it is preferred, furthermore, if at most 1 wt % of the silane monomer components are fluorine-containing silanes, based on the total weight of the precondensed heteropolysiloxane. Fluorine-containing silane components are preferably present only in trace amounts or more preferably not present in the applied precondensed heteropolysiloxane layer.

The term "aminosilane" in the sense of the present invention means that the silane in question has at least one amino group. This amino group need not be bonded directly to the silicon atom of the silyl group. Examples of aminosilanes which can be used in accordance with the invention in the preparation of the precondensed heteropolysiloxane are (6-amino-n-hexyl)(triethoxy)silane, (6-amino-n-hexyl)(trimethoxy)silane, (4-amino-3,3-dimethylbutyl)(trimethoxy)silane, $(H_2N(CH_2)_3)Si(OCH_3)_3$ ((3-aminopropyl)(trimethoxy)silane, AMMO), $(H_2N(CH_2)_3)Si(OC_2H_5)_3$ ((3-aminopropyl)(triethoxy)silane, AMEO), (3-aminoisobutyl)(trimethoxy)silane, (3-aminoisobutyl)(triethoxy)silane, (2-aminoethyl)(trimethoxy)silane, (2-aminoethyl)(triethoxy)silane, (aminomethyl)-(trimethoxy)silane, (aminomethyl)(triethoxy)silane, (N-cyclohexylaminomethyl)-(triethoxy)silane (GENIOSIL XL 926), (N-phenylaminomethyl)(trimethoxy)-silane, (6-amino-n-hexyl)(methyl)(dimethoxy)silane, (3-aminopropyl)(methyl)-(dimethoxy)silane, (3-aminopropyl)(methyl)(diethoxy)silane, (2-aminoethyl)(phenyl)(dimethoxy)silane, (2-aminoethylamino)(ethyl)(triethoxy)silane, (2-aminoethyl)(methyl)(diethoxy)silane, (2-aminoethyl)(methyl)(dimethoxy)silane, (1-aminomethyl)(methyl)(diethoxy)silane, (N-cyclohexylaminomethyl)-(methyl)(diethoxy)silane (GENIOSIL XL 924), (N-ethylaminoisobutyl)(trimethoxy)silane, (N-n-butyl-3-aminopropyl)(trimethoxy)silane, (N-n-butyl-3-aminopropyl)(triethoxy)silane, (N-n-butyl-1-aminomethyl)(triethoxy)silane, (N-n-butyl-1-aminomethyl)(trimethoxy)silane, (benzyl-3-aminopropyl)(trimethoxy)silane, (benzyl-3-aminopropyl)(triethoxy)silane, (N-phenylaminomethyl)(trimethoxy)silane (GENIOSIL XL 973), (N-phenylaminopropyl)(trimethoxy)silane, (N-formyl-3-aminopropyl)(triethoxy)-silane, (N-formyl-3-aminopropyl)(trimethoxy)silane, (N-formyl-1-aminomethyl)(methyl)-(dimethoxy)silane, (N-formyl-1-aminomethyl)(methyl)(diethoxy)silane, (N-n-butyl-3-aminopropyl)(methyl)(diethoxy)silane, (N-n-butyl-3-aminopropyl)(methyl)-(dimethoxy)silane, (N-n-butyl-1-aminomethyl)(methyl)(dimethoxy)silane, (N-butyl-1-aminomethyl)(methyl)(diethoxy)silane, (diaminoethylen-3-propyl)(triethoxy)silane, (N-(2-aminoethyl)aminoethyl)(trimethoxy)silane, (2-aminoethylaminoethyl)(triethoxy)silane, (N-(1-aminoethyl)aminomethyl)(trimethoxy)silane, (N-(1-aminoethyl)aminomethyl)-(triethoxy)silane, $H_2N(CH_2)_2NH(CH_2)_3Si(OCH_3)_3$ ((N-(2-aminoethyl)-3-aminopropyl)(trimethoxy)silane, (DAMO)), (2-aminoethylaminopropyl)(triethoxy)silane (Silquest A-1130), (2-aminoethylaminoethyl)(trimethoxy)silane, (2-aminoethylaminoethyl)(triethoxy)silane, (1-aminoethylaminopropyl)(trimethoxy)silane, (1-aminoethylaminopropyl)(triethoxy)silane, (1-aminoethylaminomethyl)(trimethoxy)-silane, (1-aminoethylaminomethyl)(triethoxy)silane, (N-cyclohexyl-3-aminopropyl)-(trimethoxy)silane, (N—(N-benzylaminoethyl)aminopropyl)(trimethoxy)silane, (3-ureidopropyl)(trimethoxy)silane, (3-ureidopropyl)(triethoxy)silane, (N-(2-aminoethyl)-3-aminopropyl)(methyl)(dimethoxy)silane, (N-(2-aminoethyl)-3-aminopropyl)(methyl)-(diethoxy)silane, $H_2N(CH_2)_2NH(CH_2)_2NH(CH_2)_3Si(OCH_3)_3$ ((triaminodiethylen-3-propyl)(trimethoxy)silane, TRIAMO), (triaminodiethylene-3-propyl)(triethoxy)silane, (triaminodiethylene-3-propyl)(trimethoxy)silane, (triaminodiethylene-3-propyl)(triethoxy)silane, (((aminoethyl)aminoethyl)aminopropyl)(trimethoxy)silane, (((aminoethyl)aminoethyl)aminopropyl)(triethoxy)silane, bis(trimethoxysilane)amine, bis(triethoxysilane)amine, bis(trimethoxysilylethyl)amine, bis(triethoxysilylmethyl)amine, bis(triethoxysilylethyl)amine, bis(trimethoxysilylpropyl)amine, bis(triethoxysilylpropyl)amine, bis(trimethoxysilylisopropyl)amine, bis(triethoxysilylisopropyl)amine, (3-trimethoxy)silylmethyl O-methyl carbamate, N-dimethoxy(methyl)silylmethyl O-methyl carbamate, triethoxysilylpropyl tert-butyl carbamates, triethoxysilylpropyl ethyl carbamates, tris(trimethoxysilylmethyl)amines, tris(trimethoxysilylethyl)amine, tris(trimethoxysilyl-n-propyl)amine, tris(trimethoxysilylisopropyl)amine, $N[(CH_2)_3Si(OC_2H_5)_3]_3$ (tris(triethoxysilylmethyl)amine, tris-AMEO), tris(triethoxysilylmethyl)amine, tris(triethoxysilylethyl)amine, tris(triethoxysilyl-n-propyl)amine, tris(triethoxysilylisopropyl)amine, $N[(CH_2)_3Si(OCH_3)_3]_3$ (tris-AMMO), $((H_5C_2O)_3Si(CH_2)_3NH(CH_2)_3Si(OC_2H_5)_3$, (bis(triethoxysilylpropyl)amine, bis-AMEO), $(H_3CO)_3Si(CH_2)_3NH(CH_2)_3Si(OCH_3)_3$ (bis(trimethoxysilylpropyl)amine, bis-AMMO), $(H_3CO)_3Si(CH_2)_3NH(CH_2)_2NH(CH_2)_3Si(OCH_3)_3$ (Bis-DAMO), $(H_3CO)_3Si(CH_2)_3NH(CH_2)_2NH(CH_2)_2NH(CH_2)_3Si(OCH_3)_3$ (bis-TRIAMO), $(H_3CO)_2(CH_3)Si(CH_2)_3NH(CH_2)_2NH(CH_2)_3Si(OCH_3)_2(CH_3)$, $(H_3CO)(CH_3)Si(CH_2)SiNH(CH_2)_2NH(CH_2)_2NH(CH_2)_3Si(OCH_3)_2(CH_3)$, $(H_3CO)_3Si(CH_2)_3NH(CH_2)_2NH(CH_2)_2NH(CH_2)_3Si(OCH_3)_3$ (Bis-DAMO), $(H_3CO)_3Si(CH_2)_3NH(CH_2)_2NH(CH_2)_2NH(CH_2)_2NH(CH_2)_3Si(OCH_3)_3$ (BiS-TRIAMO), (3-(trimethoxysilyl)methyl) (O-methyl) carbamate, (N-(dimethoxy)(methyl)silyl)methyl) (O-methyl)carbamate, (3-(triethoxysilyl)propyl) (tert-butyl) carbamate, ((triethoxysilyl)propyl) (ethyl)carbamate. In the case of further embodiments, preferably at least one aminosilane, more preferably at least 95 wt % of the aminosilanes, based on the total weight of the aminosilane components present in the precondensed heteropolysiloxane, more preferably still all of the aminosilanes, are selected from the aforementioned examples.

More particularly it is preferred if the at least one aminosilane is selected from the group of the aminosilanes of formula (I):

$$R^{a1}_{x1}R^{b1}_{y1}R^{c1}_{(4-x1-y1)}Si \qquad (I),$$

where the $R^{a1}$s independently of one another are selected from functional groups substituted by at least one nitrogen group, the functional group being selected from the group consisting of C1-C16 alkyl groups, C2-C8 alkenyl groups, C2-C8 alkynyl groups and phenyl groups, C7-C12 alkylaryl groups, and C7-C12 arylalkyl groups, the $R^{b1}$s independently of one another are selected from the group consisting of C1-C16 alkyl groups, C2-C8 alkenyl groups, C2-C8 alkynyl groups, phenyl groups, C7-C12 arylalkyl groups, and C7-C12 alkylaryl groups, the aforesaid groups being unsubstituted, the $R^{c1}$s independently of one another are selected from the group of the alkoxy groups, x1 is 1, 2 or 3, and y1 is selected from the group of the integers from 0 to (3−x1).

Preferably at least 95 wt % of the aminosilanes, based on the total weight of the aminosilane components present in the precondensed heteropolysiloxane, more preferably all the aminosilanes, are selected from the aforementioned silanes. It is preferred, furthermore, if x1=1 or 2 and y1 is selected from the group of integers from 0 to (2−x1).

If, in the embodiments of the present invention, a variable from a range of integers is selected, the stated end points of the numerical range are also included.

Unless otherwise specified in the present application, the groups stated herein such as alkyl groups, alkenyl groups, alkynyl groups, and alkoxy groups may be present in branched or unbranched form in this embodiment or in the other embodiments of the present application.

In the case of further embodiments, the $R^{a1}$s independently of one another are selected from functional groups substituted by at least one nitrogen group, the functional group being selected from the group consisting of C1-C5 alkyl groups, C2-C5 alkenyl groups, and C2-C5 alkynyl groups, and mixtures thereof, the $R^{b1}$s independently of one another are selected from the group consisting of C1-C4 alkyl groups, C2-C4 alkenyl groups, C2-C4 alkynyl groups, phenyl groups, and mixtures thereof, the aforesaid groups of $R^{b1}$ being unsubstituted, and the $R^{c1}$s independently of one another are selected from the group of the C1-C4 alkoxy groups.

It is preferred in particular for the $R^{c1}$s to be selected from the group consisting of methoxy and ethoxy.

In the case of further embodiments it is preferred if the at least one nitrogen group of $R^{a1}$ is selected from the group consisting of $-NH_{(2-r1)}R^{d1}_{r1}$ and $-(NH_{(3-s1)}R^{d1}_{s1})^+$, where $r^1$ is selected from the integers from 0 to 2 and s1 is selected from the integers from 0 to 3, and the $R^{d1}$s independently of one another are selected from the group consisting of C1-C16 alkyl groups, C2-C8 alkenyl groups, C2-C8 alkynyl groups, phenyl rings, C7-C12 alkylaryl groups, C7-C12 alkoxyalkyl groups, dialkylenediamine groups and trialkylenetriamine groups, and also saturated and unsaturated alkylenes and heteroalkylenes such as $-(CH_2)_3-$, $-(CH_3)_4-$, $-(CH_2)_5-$, $-CH=CH-CH=CH-$ or $-CH=N-(CH_2)_2-$ if r1 or s1 is ≥2, the heteroatoms in the heteroalkylenes being selected from N and O. The heteroatoms of the heteroalkylenes are preferably nitrogen atoms. Any substituents present in the aforesaid groups are preferably selected from nitrogen-containing substituents such as $-NH_{(2-t1)}R^{e1}_{t1}$ and $-(NH_{(2-u1)}R^{e1}_{u1})^+$, where t1 is selected from the integers from 0 to 2, u1 is selected from the integers from 0 to 3, and the $R^{e1}$s are selected from the group consisting of C1-C4 alkyl groups. With more particular preference the aforesaid $R^{d1}$s are unsubstituted.

In the case of further embodiments, the $R^{d1}$s are selected from the group consisting of C1-C4 alkyl groups, C2-C4 alkenyl groups, C2-C4 alkynyl groups, phenyl rings, C7-C8 alkylaryl groups, C7-C8 alkoxyalkyl groups, dialkylenediamine groups and trialkylenetriamine groups, and also saturated and unsaturated C4-C7 alkylenes and C3-C6 heteroalkylenes such as —$(CH_2)_3$—, —$(CH_3)_4$—, —$(CH_2)_5$—, —CH=CH—CH=CH— or —CH=N—$(CH_2)_2$— if r1 or s1 is 2, the heteroatoms in the heteroalkylenes being selected from N and O.

In the case of further embodiments it is preferred, furthermore, if the at least one nitrogen group of $R^{a1}$ is selected from the group consisting of —$NH_{(2-r1)}R^{d1}{}_{r1}$ and —$(NH_{(3-s1)}R^{d1}{}_{s1})^+$, where r1 is selected from the integers from 0 to 2 and s1 is selected from the integers from 0 to 3, and the $R^{d1}$s independently of one another are selected from the group consisting of unsubstituted and substituted C1-C8 alkyl groups, preferably C1-C4 alkyl groups, the substituents being selected from the group consisting of —$NH_{(2-t1)}R^{e1}{}_{t1}$ and —$(NH_{(3-u1)}R^{e1}{}_{u1})^+$, where t1 is selected from the integers from 0 to 2 and u1 is selected from the integers from 0 to 3, and the $R^{e1}$s independently of one another are selected from the group consisting of unsubstituted C1-C4 alkyl groups and C1-C4 aminoalkyl groups.

In the case of further embodiments it is preferred if at least one aminosilane is selected from the group consisting of aminoalkyltrialkoxysilanes, bis(aminoalkyl)dialkoxysilanes, (alkyl)(aminoalkyl)(dialkoxy)silane, ((aminoalkyl)aminoalkyl)(trialkoxy)silanes, bis(trialkoxysilylalkyl)amines, tris(trialkoxyalkyl)amines, bis-N,N'-(trialkoxysilylalkyl)alkylenediamines, bis-N,N'-(trialkoxysilylalkyl)dialkylenetriamines, the alkyl groups independently of one another being selected from the group consisting of methyl group, ethyl group, propyl groups, and butyl groups, and the alkoxy groups independently of one another being selected from the group consisting of methoxy group and ethoxy group. Particularly preferred is the selection of at least one aminosilane from the group consisting of aminoalkyltrialkoxysilanes, ((aminoalkyl)aminoalkyl)(trialkoxy)silanes, and bis(trialkoxysilylalkyl)amines.

In accordance with the present invention, a distinction is made between alkylsilanes and the silanes functionalized in any of a wide variety of ways, such as aminosilanes. The term "alkylsilane" in the sense of the present invention does not encompass functionalized silanes such as aminosilanes, even if these samples, for example, may have an unsubstituted aminoalkyl group as well as an aminoalkyl group. Examples of the at least one alkylsilane are (methyl)(trialkoxy)silane, (ethyl)(trialkoxy)silane, (n-propyl)(trialkoxy)silane, (isopropyl)(trialkoxy)silane, (n-butyl)(trialkoxy)silane, (isobutyl)(trialkoxy)silane, (n-octyl)(trialkoxy)silane, (isooctyl)(trialkoxy)silane, (decyl)(trialkoxy)silane, (dodecyl)(trialkoxy)silane, (hexadecyl)(trialkoxy)silane, (dimethyl)(dialkoxy)silane, with alkoxy standing for methoxy, ethoxy, and mixtures thereof. With preference at least one alkylsilane, preferably at least 95 wt % of the alkylsilanes, based on the total weight of the alkylsilane components present in the precondensed heteropolysiloxane, more preferably all the alkylsilanes, is or are selected from the aforesaid examples.

In the case of further embodiments it is preferred if the at least one alkylsilane has a structure of formula (II)

$$R^{a2}{}_{x2}R^{b2}{}_{(4-x2)}Si \qquad (II),$$

where the $R^{a2}$s independently of one another are selected from the group of the unsubstituted C1-C16 alkyl groups, the $R^{b2}$s independently of one another are selected from the group of the alkoxy groups, and x2 is selected from 1 and 2.

Preferably at least 95 wt % of the alkylsilanes, based on the total weight of the alkylsilane components present in the heteropolysiloxane, more preferably all the alkylsilanes, are selected from the aforesaid silanes.

In the case of further embodiments it is preferred if the $R^{a2}$s independently of one another are selected from the group of the unsubstituted C1-C8 alkyl groups, and the $R^{b2}$s independently of one another are selected from the group of the C1-C4 alkoxy groups.

In the case of further embodiments it is preferred if at least one Rae of the at least one alkylsilane of formula (II) is selected from the group of the unsubstituted C1-C3 alkyl groups.

More particularly it is preferred if the $R^{c2}$s are selected from the group consisting of methoxy and ethoxy.

In the case of further embodiments it is preferred if the $R^{a2}$s are selected from the group of the C1-C8 alkyl groups, more preferably the C1-C6 alkyl groups, and more preferably still the C1-C4 alkyl groups, the aforesaid groups being unsubstituted. Examples of such alkyl chains are methyl, ethyl, isopropyl, n-propyl, n-butyl, isobutyl, tert-butyl, hexyl, and octyl.

In the case of further embodiments it is preferred if the at least one vinylsilane component is selected from the group consisting of (vinyl)(trialkoxy)silane, (vinyl)(methyl)(dialkoxy)silane, (vinyl)(tris(methoxyethoxy))silane, (vinyl)tris(2-methoxyethoxy)silane, (vinyl)(triacetoxy)silane, (((vinylbenzylamino)ethylamino)propyl)(trialkoxy)silane, (allyl)(trialkoxy)silane, and (allyl)(triethoxy)silane, where alkoxy stands for methoxy, ethoxy, and mixtures thereof, preferably for methoxy. With preference at least one vinylsilane, preferably at least 95 wt % of the vinylsilanes, based on the total weight of the vinylsilane components present in the precondensed heteropolysiloxane, more preferably more preferably all the vinylsilanes, is or are selected from aforesaid examples.

In the case of further embodiments it is preferred if the at least one vinylsilane has a structure of formula (III)

$$R^{a3}{}_{x3}R^{b3}{}_{y3}R^{c3}{}_{(4-x3-y3)}Si \qquad (III),$$

where the $R^{a3}$s independently of one another are selected from the group of the unsubstituted C2-C16 vinyl groups, the $R^{b3}$s independently of one another are selected from the group of the unsubstituted C1-C16 alkyl groups, the $R^{c3}$s independently of one another are selected from the group of the alkoxy groups,
x3 is selected from 1 and 2, and
y3 is selected from the group of the integers from 0 to (2−x3).

Preferably at least 95 wt % of the vinylsilanes, based on the total weight of the vinylsilane components present in the precondensed heteropolysiloxane, more preferably more preferably all the vinylsilanes, are selected from the aforesaid silanes.

In the case of further embodiments it is preferred if the $R^{a3}$s independently of one another are selected from the group of the unsubstituted C2-C7 vinyl groups, the $R^{b3}$s independently of one another are selected from the group of the unsubstituted C1-C8 alkyl groups, and the $R^{c3}$s independently of one another are selected from the group of the C1-C4 alkoxy groups.

More particularly it is preferred if the $R^{b3}$s are selected from the group consisting of methoxy and ethoxy.

In the case of further embodiments it is preferred if the at least one arylsilane is selected from the group consisting of (phenyl)(trialkoxy)silane, (phenyl)(methyl)(dialkoxy)silane, (diphenyl)(dialkoxy)silane, (phenyl)(methyl)(dialkoxy)silane, and (benzyl-2-aminoethyl-3-aminopropyl)(trialkoxy)silane, where alkoxy stands for methoxy, ethoxy, and mixtures thereof, preferably for methoxy.

In the case of further embodiments it is preferred if the at least one arylsilane has a structure of formula (IV)

$$R^{a4}_{x4}R^{b4}_{y4}R^{c4}_{(4-x4-y4)}Si \qquad (IV),$$

where the $R^{a4}$s independently of one another are selected from the group consisting of phenyl groups, unsubstituted C7-C12 alkylaryl groups, and unsubstituted C7-C12 arylalkyl groups,
the $R^{b4}$s independently of one another are selected from the group of the unsubstituted C1-C16 alkyl groups,
the $R^{c4}$s independently of one another are selected from the group of the alkoxy groups,
x4 is selected from 1 and 2, and
y4 is selected from the group of the integers from 0 to (2−x4).

Preferably at least 95 wt % of the arylsilanes, based on the total weight of the arylsilane components present in the precondensed heteropolysiloxane, more preferably all the alkylsilanes, are selected from the aforesaid silanes.

In the case of further embodiments it is preferred if the $R^{a4}$s are selected from the group consisting of phenyl groups, C7-C10 unsubstituted alkylaryl groups, and unsubstituted C7-C10 arylalkyl groups, the $R^{b4}$s are selected from the group of the unsubstituted C1-C8 alkyl groups, and the $R^{c4}$s independently of one another are selected from the group of the C1-C4 alkoxy groups.

More particularly it is preferred if the $R^{c4}$s are selected from the group consisting of methoxy and ethoxy.

Examples of acryloylsilanes are (methacryloyloxymethyl)(methyl)(dialkoxy)silane, (methacryloyloxymethyl)(trialkoxy)silane, (3-methacryloyloxypropyl)(trialkoxy)silane, (3-methacryloyloxyisobutyl)(trialkoxy)silane, (3-methacryloyloxypropyl)(methyl)-(dialkoxy)silane, (1-methacryloyloxymethyl)(trialkoxy)silane, (3-acryloxypropyl)(trialkoxy)silane, and (acryloxymethyl)(trialkoxy)silane, where alkoxy stands for methoxy or ethoxy. One particularly preferred example is (methacryloyloxypropyl)(trimethoxy)silane (MEMO).

In the case of further embodiments it is preferred if at least one acryloylsilane has a structure of formula (V)

$$R^{a5}_{x5}R^{b5}_{y5}R^{c5}_{(4-x5-y5)}Si \qquad (V),$$

where the $R^{a5}$s are selected from the group consisting of unsubstituted C3-C10 acryloyl groups and unsubstituted ((C3-C7-acryloyloxy)C1-C5-alkyl)trialkoxy, the $R^{b5}$s are selected from the group of the unsubstituted C1-C16 alkyl groups, the $R^{c5}$s are selected from the group of the alkoxy groups,
x5 is selected from 1 and 2, and
y5 is selected from the group of the integers from 0 to (2−x5).

Preferably at least 95 wt % of the acryloylsilanes, based on the total weight of the acryloylsilane components present in the precondensed heteropolysiloxane, more preferably all the acryloylsilanes, are selected from the aforesaid silanes.

In the case of further embodiments the $R^{a5}$s are selected from the group of the unsubstituted C3-C7 acryloyl groups, the $R^{b5}$s are selected from the group of the unsubstituted C1-C8 alkyl groups, and the $R^{c5}$s are selected from the group of the unsubstituted C1-C4 alkoxy groups.

More particularly it is preferred if the $R^{c5}$s are selected from the group consisting of methoxy and ethoxy.

Examples of epoxysilanes are 3-glycidyloxypropyltrialkoxysilane, 3-glycidyloxypropyltrialkoxysilane, glycidyloxypropylmethyldialkoxysilane, and (beta-(3,4-epoxycyclohexyl)ethyl)(trialkoxy)silane, where alkoxy stands for methoxy, ethoxy or propoxy.

It has emerged that the use of relatively large amounts of epoxysilane components, as for example in typically utilized wet coating systems such as melamine systems, is a disadvantage. On the other hand, in powder coating systems, for example, it proved not noticeably disadvantageous, or even advantageous. Particularly in connection with ferromagnetic pigments, the use of a precondensed heteropolysiloxane comprising significant amounts of epoxysilanes is typically not problematic or is even desirable. In the case of further embodiments, however it is preferred if the precondensed heteropolysiloxane comprises less than 10 wt %, more preferably more preferably less than 3 wt %, more preferably still less than 1 wt % of epoxysilane components. The latter is the case especially when ferromagnetic pigments, which are intended primarily for use in powder coating systems, are to be provided for a broader field of application.

In the case of further embodiments it is preferred if the precondensed heteropolysiloxane comprises at least one further monomer selected from the group consisting of tetramethoxysilane, tetraethoxysilane, tetrapropoxysilane, and mixtures thereof.

In the case of further embodiments, the precondensed heteropolysiloxane preferably comprises at least one silane of formula (VI)

$$R^{a6}_{4}Si \qquad (VI),$$

where the $R^{a6}$s independently of one another are selected from the group of the alkoxy groups. Preferably, the $R^{a}$s independently of one another are selected from the group of the C1-C4 alkoxy groups.

In the case of further embodiments it is preferred if at least 32 wt % of the monomer components, preferably at least 36 wt % of the monomer components, more preferably still at least 41 wt % of the monomer components which make up the precondensed heteropolysiloxane are selected from the aminosilanes, based in each case on the total weight of the precondensed heteropolysiloxane.

In the case of further embodiments it is preferred, moreover, if the fraction of aminosilane components in the precondensed heteropolysiloxane is at most 95 wt %, more preferably at most 89 wt %, more preferably still at most 86 wt %, based in each case on the total weight of the precondensed heteropolysiloxane.

In the case of further embodiments it is preferred in particular if the fraction of aminosilane components in the precondensed heteropolysiloxane is in the range from 32 wt % to 95 wt %, more preferably in the range from 36 wt % to 89 wt %, more preferably still in the range from 41 wt % to 86 wt %, based in each case on the total weight of the precondensed heteropolysiloxane.

In the case of further embodiments it is preferred if at least 12 wt % of the monomer components, more preferably at least 17 wt % of the monomer components, more preferably still at least 23 wt % of the monomer components of the precondensed heteropolysiloxane are selected from the alkylsilanes, based in each case on the total weight of the precondensed heteropolysiloxane.

In the case of further embodiments it is preferred, furthermore, if at most 76 wt % of the monomer components, more preferably at most 72 wt % of the monomer components, more preferably still at most 69 wt % of the monomer components of the precondensed heteropolysiloxane are selected from alkylsilanes, based in each case on the total weight of the precondensed heteropolysiloxane.

In the case of further embodiments it is preferred in particular if the fraction of alkylsilane components in the precondensed heteropolysiloxane is in the range from 12 wt % to 76 wt %, more preferably in the range from 17 wt % to 72 wt %, more preferably still in the range from 23 wt % to 69 wt %, based in each case on the total weight of the precondensed heteropolysiloxane.

In the case of further embodiments it is preferred if the precondensed heteropolysiloxane consists to an extent of at least 87 wt %, more preferably at least 93 wt %, more preferably still at least 97 wt % of monomer components which are selected from aminosilanes and alkylsilanes.

In the case of further preferred embodiments, the aforesaid quantity figures relating to the alkylsilane components and aminosilane components pertain to the specific groups of alkylsilanes and aminosilanes, as set out above. This is the case, for example, when at least 95 wt % of the alkylsilanes have a structure of formula (II)

$$R^{a2}_{x2}R^{b2}_{(4-x2)}Si \qquad (II),$$

where the $R^{a2}$s independently of one another are selected from the group of the unsubstituted C1-C16 alkyl groups, the $R^{b2}$s independently of one another are selected from the group of the alkoxy groups, and x2 is selected from 1 and 2. Preferably at least 95 wt % of the alkylsilanes, based on the total weight of the alkylsilane components present in the precondensed heteropolysiloxane, more preferably all the alkylsilane components, are selected from the aforesaid silanes.

The pigments coated with the precondensed heteropolysiloxane surprisingly exhibit improved orientation in wet coating materials, resulting in better lightness flops.

The precondensed heteropolysiloxane optionally employed comprises at least one aminosilane component and at least one silane component which is selected from the group consisting of alkylsilanes, vinylsilanes, and arylsilanes. The condensation of corresponding monomers, oligomers and/or polymers for producing precondensed heteropolysiloxanes used is accomplished by means of methods known to the skilled person, as are disclosed for example in U.S. Pat. Nos. 5,808,125 A, 5,679,147 A, and 5,629,400 A. Furthermore, various precondensed heteropolysiloxanes are also available commercially. Preferred precondensed heteropolysiloxanes are available for example from Evonik Industries AG, 45128 Essen, Germany, under the trade names Dynasylan Hydrosil 2627, Dynasylan Hydrosil 2776, Dynasylan Hydrosil 2909, Dynasylan 1146, and Dynasylan Hydrosil 2907. Particularly preferred water-based precondensed heteropolysiloxanes are Dynasylan Hydrosil 2627, Dynasylan Hydrosil 2776, Dynasylan Hydrosil 2907, and Dynasylan Hydrosil 2909.

According to one preferred variant of the invention, the precondensed heteropolysiloxane is selected from the group consisting of Dynasylan Hydrosil 2627, Dynasylan Hydrosil 2776, Dynasylan Hydrosil 2909, Dynasylan 1146, Dynasylan Hydrosil 2907, and mixtures thereof.

The precondensed heteropolysiloxane is used preferably in the form of an aqueous formulation. In particular, formulations preferably have a concentration of precondensed heteropolysiloxane in the range from 5 to 50 wt %, based on the total weight of the formulation.

The precondensed heteropolysiloxane may be applied by means of methods known to the skilled person. One preferred method, being associated in particular with very low cost and effort and with outstanding results, is the exposure of the pigment to be coated to the action of an aqueous solution of the precondensed heteropolysiloxane. The action time in this case ought to be between 15 minutes and 240 minutes.

In the case of further embodiments it is especially preferred if the application of the heteropolysiloxane layer is not followed by any step of curing, more particularly thermal curing, of the siloxane layer.

In the case of further embodiments, the precondensed heteropolysiloxane has less than 0.5 wt % of alcohols which, during the preparation of the precondensed heteropolysiloxane, are released as a consequence of hydrolysis and/or condensation.

Surprisingly it has emerged, furthermore, that preferably the precondensed heteropolysiloxane is substantially completely, preferably completely, hydrolyzed. In spite of the reduced possibility for further reaction or crosslinking, precondensed heteropolysiloxanes of this kind achieve predominantly better results.

The precondensed heteropolysiloxanes used in accordance with the invention preferably have a volatile organic solvents content of less than 0.3 wt %, based on the total weight of the precondensed heteropolysiloxane.

The precondensed heteropolysiloxane is used preferably in the form of an aqueous formulation. For the majority of applications it is typically preferred if the aqueous formulation comprising the precondensed heteropolysiloxane includes amounts as small as possible of VOCs (volatile organic compounds) such as of the alcohol normally formed in the reaction of the silane monomers. In the case of further embodiments it is preferred if the aqueous formulations contain less than 5 wt %, preferably less than 1 wt %, more preferably less than 0.5 wt %, more preferably still less than 0.1 wt %, of VOCs, based in each case on the weight of the aqueous formulation. Employed ideally are aqueous formulations in which there are no VOCs present.

In the case of further embodiments, the metal oxide of the coating layer to which the precondensed heteropolysiloxane is applied is selected substantially, preferably completely, from the group consisting of silicon oxide, aluminum oxide, boron oxide, zirconium oxide, cerium oxide, iron oxide, titanium oxide, chromium oxide, tin oxide, molybdenum oxide, their oxide hydrates, their hydroxides, and mixtures thereof. With particular preference the metal oxides of the invention are selected from the group consisting of silicon oxide, aluminum oxide, and mixtures thereof, the term "metal oxide" also encompassing oxide hydrates and hydroxides. Having proven advantageous more particularly is the use of silicon oxides such as silicon dioxide, silicon hydroxide and/or silicon oxide hydrate.

Particularly high-grade properties, in terms for example of the stability, are achieved through the combination of the inorganic/organic hybrid layer with the precondensed heteropolysiloxane. In the case of further embodiments it is preferred if the precondensed heteropolysiloxane is applied to the inorganic/organic hybrid layer of the invention. More particularly it is preferred if the aforesaid inorganic/organic hybrid layer comprises silicon oxide, silicon hydroxide, silicon oxide hydrate or mixtures thereof. The metal oxide present in the inorganic/organic hybrid layer preferably consists substantially of silicon oxide, silicon hydroxide, silicon oxide hydrate or mixtures thereof.

It proved particularly advantageous, furthermore, if the precondensed heteropolysiloxane was applied as the outermost layer of the pigment of the invention. Thus pigments wherein the precondensed heteropolysiloxane had contact with the surrounding medium exhibited particularly high compatibility in a multiplicity of coating materials. In this case, preferably, the precondensed heteropolysiloxane is applied as the outermost layer to an inorganic/organic hybrid layer of the invention.

According to further variants of the present invention it is preferred, furthermore, to optimize the coating as a whole in order to provide improved results for specific applications, for example.

In the case of further embodiments, the coating of the pigments of the invention, more particularly of the metallic effect pigments, preferably has an average thickness in a range from 20 nm to 160 nm, more preferably in a range from 25 nm to 135 nm, determined using scanning electron microscopy.

The layer thicknesses of the coating, and also of the individual coating layers, are determined for example by means of SEM micrographs on suitable ground sections. In this case the pigments are applied in a varnish, and the varnish is cured. Attention should be paid here to extremely good orientation of the platelets in the application medium. The cured varnish is subsequently ground and, after appropriate sample preparation, the ground section is viewed in SEM. Particles selected for the count are only those which exhibit a good plane-parallel orientation. With this method, poorly oriented platelets result in a high error because of the unknown viewing angle. The coatings exhibit very good contrast to the metal core. If it is not possible to differentiate readily the layer thicknesses of the metal oxide layer and of the polymeric layer, it is possible to use spatially resolved EDX analyses before the layer thicknesses are measured. The term "average layer thickness" in the sense of the invention refers to the arithmetic mean of the layer thicknesses of the layers of at least 30 metal pigments, preferably 40 metal pigments. If the coating is uneven, the arithmetic mean of the thinnest and thickest areas of the coating of the respective particle is formed. Individual, substantial deviations deriving, for example, from the inclusion of already coated finely divided pigments in the coating are not considered when determining the average layer thickness.

In the case of further embodiments it is preferred if the thickness of the inorganic/organic hybrid layer is at least 40%, more preferably at least 60%, more preferably still at least 85% of the total thickness of the coating. Determining the total thickness of the coating is done preferably by SEM, looking at the entire coating over the metallic substrate. Not included of course are any lightly adhering subsequent coatings or constituents, for example, of a varnish composition in which the pigments were formulated. Such residues are removed prior to the measurement, by washing of the pigments in solvents known to the skilled person.

The pigments of the invention may take the form of a dry product, paste or suspension. Dry products in the sense of the present invention are, for example, powders and granules. Such forms have shown, for example, the advantage that there is no need for additional solvents to be transported and stored, such solvents possibly at the same time giving rise to incompatibility in later applications. Pastes and suspensions, on the other hand, do exhibit such disadvantages, but may be easier to handle, since, for example, there is reduction in or prevention of dust formation on removal and on transfer.

The present invention further relates to a method for producing coated pigments, the method comprising the following steps:
  i) reacting at least one metal oxide reactant, at least one reactant of an organic polymer, and at least one network former in a liquid phase to form a coating composition,
  ii) applying the coating composition to metallic substrates to form an inorganic/organic hybrid layer,
the inorganic/organic hybrid layer comprising at least one inorganic network comprising at least one metal oxide and at least one organic polymer, and the inorganic network and the organic polymer being joined covalently to one another, the at least one metal oxide being selected from oxides, hydroxides, and oxide hydrates of the metals and semimetals, and not being an oxidation product of the metallic substrate,
the network former being joined at least partially to the metal oxide and to the organic polymer,
the ratio of the amount of metal oxide of the coating to the specific surface area of the uncoated metal pigment being in a range from 16.1 mg/m$^2$ to 25 mg/m$^2$, and
the ratio of the amount of organic polymer of the inorganic/organic hybrid layer to the specific surface area of the uncoated metal pigment being in a range from 3.9 mg/m$^2$ to 10.1 mg/m$^2$. The aforementioned amount of metal oxide in the coating is based on the coating without any applied subsequent coatings. The metallic substrates are preferably platelet-shaped metallic substrates. Steps i) and ii) here may run separately in terms of time, simultaneously, or partially simultaneously.

The reaction of the reactants of the inorganic/organic hybrid layer must of course take place at least partially simultaneously in order for the hybrid layer of the invention to form. In this case the network former, the reactant of the metal oxide, and the reactant of the organic polymer may be mixed with one another in any order. It is necessary, however, to ensure that the covalent bonds between the individual constituents can be formed. The reactants are preferably first mixed with one another, before the reaction is initiated for example by addition of an acid, a base or a specific catalyst.

The metallic substrates here may already have been introduced initially or may only be added during or after the reaction of the coating constituents. In that case the coating constituents may also be added over a defined time period in variable quantity in order to obtain, in certain embodiments, a greater fraction of metal oxide near to the surface of the metallic substrate and/or near to the surface of the inorganic/organic hybrid layer. In the case of further embodiments, furthermore, there is an increased fraction of organic polymer close to the surface of the metallic substrate and/or close to the surface of the inorganic/organic hybrid layer. In accordance with the invention, an inorganic/organic mixed layer does not mean that only a covalent connection is generated between discrete layers of metal oxide and organic polymer. Through deposition of metal oxide as a coating on the metallic substrate in a first step, followed by the addition of network former and of the reactant of the organic polymer, or vice versa, for example.

In the case of further embodiments it is preferred if the weight ratio of the amount of metal oxide in the coating to the amount of organic polymer in the inorganic/organic hybrid layer of the coated metal pigments is in a range from 2.5:1 to 9.0:1, more preferably in a range from 3.0:1 to 8.1:1, more preferably still in a range from 3.3:1 to 6.7:1.

Furthermore, according to further embodiments, it is preferred if the ratio of the amounts of substance in moles of network former to organic polymer of the inorganic/organic hybrid layer of the coated metal pigments is in the range from 1:10 to 5:10, more preferably in the range from 1.2:10 to 4:10, more preferably still in the range from 1.4:10 to 3.5:10.

In the case of further embodiments, the inorganic/organic hybrid layer is applied to the uncoated metallic substrate. In this case, "uncoated" means that the metallic substrate has no enveloping coating, but instead, for example, has only residues of grinding assistants in the case of platelet-shaped metallic substrates, or additives for reducing or preventing agglomeration.

It has further proven advantageous in the case of the pigments of the invention to use precondensed heteropolysiloxanes, which are applied to a metal oxide-containing coating layer. The precondensed heteropolysiloxanes are added preferably after the construction of at least one inorganic/organic hybrid layer.

In the case of further embodiments it is preferred in particular if the precondensed heteropolysiloxanes are added after the step of constructing the inorganic/organic hybrid layer. In this case it is advantageous if the reaction of the reactants of the inorganic/organic mixed layer is at least largely ended before the precondensed heteropolysiloxane is applied. The "largely ended" preparation of the inorganic/organic coating layer is understood in the sense of the present invention to mean that at most 30 wt % of the reactants of the coating are still reactive. Preferably less than 15 wt %, more preferably less than 5 wt %, of the reactants are still reactive. The amount is determined on the basis of the reactive reactant quantities still present in solution. This proves, surprisingly, to be extremely advantageous, since it allows a very thin coating construction to be realized. In this context, no marked diminishment in the advantageous properties in terms, for example, of the stability were observed, as compared for example with a construction having a metal oxide layer in between. At the same time, a construction of this kind results in improved optical properties.

In the case of further embodiments, the reaction temperature in steps i) and/or ii) is preferably in a range from 0° C. to 180° C., more preferably from 40° C. to 120° C., more preferably still in a range from 60° C. to 100° C.

Furthermore, in the case of further embodiments, it is preferred if the reaction of the reactants of the inorganic/organic hybrid layer is carried out either
a) first at a pH of at most 6.8 and later at a pH of at least 7.2 or
b) first at a pH of at least 7.2 and later at a pH of at most 6.8.

Hence it emerged, surprisingly, that changing the pH during the reaction of the constituents of the inorganic/organic coating resulted, for example, in an improved stability on the part of the coating.

In the case of further embodiments it is preferred, furthermore, if the pH initially in the case of a) or later in the case of b) is in the range from 2.5 to 6.8, more preferably initially in the case of a) or later in the case of b) in the range from 3.5 to 6.5, more preferably still in the range from a) initially or in the case of b) later at 4 to 6.

In the case of further embodiments it is preferred, furthermore, if the pH later in the case of a) or initially in the case of b) is in the range from at 7.2 to 11.5, more preferably later in the case of a) or initially in the case of b) is in the range from 7.5 to 11, more preferably still later in the case of a) or initially in the case of b) is in the range from 8 to 10.2.

The acids and bases employed in this case serve in particular as a catalyst for the hydrolysis and condensation of the metal oxide.

It was further observed that the use of specific acids to adjust the pH proved particularly advantageous. In the case of further embodiments, acids are used which are selected from the group of the organic acids, preferably from the group consisting of formic acid, acetic acid, propionic acid, oxalic acid, malonic acid, maleic acid, succinic acid, anhydrides of the stated acids, and mixtures thereof, more preferably from the group consisting of formic acid, acetic acid, oxalic acid, and mixtures thereof. In this way it has been possible, surprisingly, to construct particularly homogeneous coatings.

Where the production of the coatings is to take place as inexpensively as possible, on the other hand, inorganic acids have proven advantageous, more particularly mineral acids such as hydrochloric acid, sulfuric acid, nitric acid, phosphoric acid, and mixtures thereof.

It was further observed that an improved layer construction can typically be achieved by using a base selected from the group consisting of organic bases, ammonia, hydrazine, and mixtures thereof can be achieved. The organic bases are preferably selected from amines such as primary, secondary, and tertiary amines. Examples are dimethylethanolamine (DMEA), monoethanolamine, diethanolamine, triethanolamine, ethylenediamine (EDA), tert-butylamine, monomethylamine, dimethylamine, trimethylamine, monoethylamine, diethylamine, triethylamine, pyridine, pyridine derivatives, aniline, aniline derivative, choline, choline derivatives, urea, urea derivatives, hydrazine derivatives, and mixtures thereof.

In the case of further embodiments it is preferred, on the other hand, for at least one base to be used that is selected from the inorganic bases, preferably from inorganic bases which are selected from the group consisting of ammonia, hydrazine, sodium hydroxide, potassium hydroxide, ammonium carbonate, ammonium hydrogen carbonate, sodium carbonate, sodium hydrogen carbonate, potassium carbonate, potassium hydrogen carbonate, and mixtures thereof.

In the case of further embodiments it is especially preferred if the reaction of the reactants of the inorganic/organic hybrid layer takes place initially at a pH of less than 7 and later at a pH of more than 7.

In the case of further embodiments, the reaction of the reactants of the inorganic/organic hybrid layer is initially started before the metallic substrates are added. This has proven, surprisingly, to be advantageous in certain cases, since then the reaction of the reactants of the inorganic/organic hybrid layer, which has already partially concluded, still always allowed very reliable coatings to be obtained. Hence this method variant is particularly suitable for the coating of sensitive metallic substrates and for the reaction of slow-to-react reactants of the inorganic/organic hybrid layer, since the metallic substrates need not be present from the start of the reaction of the reactants of the inorganic/organic hybrid layer.

For the majority of cases, on the other hand, it proved advantageous to carry out the reaction of the reactants of the inorganic/organic hybrid layer in the presence of the metallic substrates. In particular, coatings obtained by this means appear to still be more uniform and more stable.

In the case of further embodiments, the method comprises the application of at least one further coating layer comprising at least one metal oxide.

In the case of further embodiments, the method comprises the application at least one further coating layer which consists substantially of at least one organic polymer. The layer in question is disposed preferably between the inorganic/organic hybrid layer and the metallic substrate.

In the case of further embodiments, it is preferred, furthermore, if monomers used for the at least one organic polymer are substantially monomers which were equipped with at least one functionality selected from the group consisting of amino groups, thiol groups, epoxy groups, acrylate groups, methacrylate groups, vinyl groups, allyl groups, alkenyl groups, alkynyl groups, carboxyl groups, carboxylic anhydride groups, isocyanate groups, cyanate groups, ureido groups, and carbamate groups, more preferably from the group consisting of acrylate groups, methacrylate groups, hydroxyl groups, carboxyl groups, and carboxylic anhydride groups, more preferably still from the group consisting of acrylate groups and methacrylate groups. Preferably at least 95 wt %, more preferably at least 99 wt %, of the monomer constituents present in the organic polymer are selected from such monomers, based in each case on the total weight of the monomer constituents.

In the case of further embodiments, the specified coating layers are applied in a one-pot reaction.

In the case of further embodiments, at least one tetraalkoxysilane or the oligomer of at least one tetraalkoxysilane is used in the production of the inorganic/organic hybrid layer. The alkoxy groups of the tetraalkoxysilane may be selected independently of one another, for example, from the group of the C1-C4 alkoxy groups. However, particularly preferred tetraalkoxysilanes are represented by tetralkoxy groups having at least 3, preferably at least 4, identical alkoxy groups. The tetraalkoxysilanes are preferably selected from the group consisting of tetraethoxysilane and oligomers of tetraethoxysilane.

In the case of further embodiments, an organofunctional silane is used in the production of at least one inorganic/organic hybrid layer.

In the case of further embodiments, a liquid phase selected is a solvent from the group consisting of water, alcohols, glycol ethers, ketones, acetate esters, white spirit, and mixtures thereof.

According to one further variant, the present invention relates to a coated pigment, more particularly a coated metallic effect pigment with metal core, which has been produced in accordance with the method of the invention or one of its embodiments. In this case it is preferred more particularly for it to have been produced according to one of the methods as described in claims 14 to 16 and aspects 23 to 32.

The invention further relates to coated materials which comprises pigments coated in accordance with the invention, especially those as specified in claims 1 to 13 or aspects 1 to 22, or produced by means of the method according to any of claims 14 to 16 or any of aspects 23 to 32.

In the case of further embodiments, the coating material is selected from the group consisting of waterborne coatings, solventborne coatings, and powder coatings. A particularly preferred coating material for the ferromagnetic pigments coated in accordance with the invention are powder coatings.

The invention further relates to an article which comprises metal pigments with coating, also referred to as coated metal pigments, according to any of claims 1 to 13 or aspects 1 to 22.

The present invention further relates to the use of the pigments of the invention in a cosmetic, a plastic or a coating material. Examples of the coating materials are surface coatings, such as wet coatings and powder coatings, and colors, such as printing inks and architectural coatings.

The pigments of the invention may be incorporated in particular into coating materials selected, for example, from the group consisting of wet coatings such as water-based coatings and solventborne coatings, powder coatings, coil coating formulations, and printing inks. Further, the pigments of the invention are outstandingly suitable for use in plastics or cosmetics. One particularly preferred group of coating materials are colors such as printing inks and liquid inks, wet coatings and powder coatings. One particular field of application of the printing inks and liquid inks is the field of security printing inks.

The present invention further relates to the use of the pigments of the invention in water-based and solvent-based coatings. Such coatings are used, for example, in the automobile sector and industrial sector. In the case of application in water-based systems, the pigment of the invention may be slurried in water or customary co-solvents, such as butyl glycol, for example. Furthermore, the pigment of the invention may also be incorporated directly into the water-based application medium. Similar comments apply to use in solvent-based coatings. The pigments of the invention are notable here for outstanding dispersing behavior.

The invention relates, furthermore, to the use of the pigments of the invention in powder coatings. Powder coatings are used, for example, in the industrial line manufacture for the coating of electrically conductive and temperature-stable materials. The powder coating for application is present in this case as a solid and solvent-free powder. Furthermore, the powder coatings used as a primer or single-coat topcoat are almost completely recyclable. The environmentally friendly and diversely employable powder coatings comprise binders, pigments, fillers and crosslinkers, and also, optionally, additives. A binder is understood as the definition familiar to the skilled person. In other words, the binder comprises not only the film former but also nonvolatile auxiliaries such as plasticizers, fillers and/or curing agents, for example. The fine powder coatings are generally applied electrostatically, before being cured by baking or by radiative energy.

For the pigmentation of the powder coatings it is possible among others to use platelet-shaped pigments. In the case of powder coatings produced by mixing methods, however, it may prove to be a problem that, because of the shearing forces which act on the pigment platelets in the course of the extrusion and grinding operation, the pigment platelets may be damaged or destroyed. As a result, there may be adverse effects in particular on the gloss and hence also on the optical qualities of applications pigmented in this way.

For this reason, for example, in a dry-blend process, the metallic effect pigments are admixed to the base powder coating only after grinding has taken place. A disadvantage of this, however, is that a possible separation of pigment and powder coating occurs during coating application, owing to the difference in charging behavior of the individual coating constituents. A consequence of this is an irregular optical effect as a result of depletion or accumulation of pigment in the powder coating during powder coating application. Further, the separation of pigment and binder leads to an altered composition of the "overspray", in other words of the fraction of powder coating material which is sprayed past the article to be coated, and which ought to be recycled for reasons of cost. Alternatively, the so-called bonding process is used, in which the pigment is fixed to the particles of the basecoat by heating. The production of such bonding powder coatings, however, is relatively costly. The powder coatings that are presently most cost-efficient are produced by mixing processes. In such processes, the pigments are mixed together with all the other raw materials, extruded, and ground.

The pigments of the invention may additionally be used in a coil coating process. This process is notable for its high environmental friendliness. Coating and drying in this case take place continuously within a closed system; in the no-rinsed process, moreover, there is no rinsing to remove chemical residues. Furthermore, by means of an optimized operating regime, it is possible to achieve a degree of application efficiency of virtually 100%; otherwise, with the majority of coating processes, for example, there are relatively large losses as a result of the overspraying. Since in the case of coil coating, however, the coating is baked at temperatures of 240 to 280° C., only particularly stable pigments can be used for this process.

The pigments of the invention may be employed, furthermore, in printing inks. Examples of such printing inks are gravure printing, screen or flexographic printing inks. The pigments of the invention are also particularly suitable for water-based coatings (waterborne coatings) and exterior applications.

Gravure, flexographic or screen printing inks contain solvents or solvent mixtures. One of the purposes of these solvents or mixtures is to dissolve the binders, but another is to set important application properties of the printing inks, such as the viscosity or the drying speed, for example. Low-boiling solvents are typically employed, whereas higher-boiling solvents serve in smaller amounts to adjust the drying speed.

Besides solvents, an ink may comprise various further constituents, such as reactive diluents and photoinitiators in the case of radiation-curable printing inks, for example; binders such as, for example, nitrocellulose, ethylcellulose, hydroxyethylcellulose, acrylates, polyvinyl butyrals, aliphatic and aromatic polyurethanes, and polyureas; fillers such as calcium carbonate, aluminum oxide hydrate, aluminum silicate, and magnesium silicate, waxes such as polyethylene waxes, oxidized polyethylene waxes, petroleum waxes, and ceresin waxes; fatty acid amides, plasticizers; dispersing assistants, fatty acids, and antisettling agents.

The present invention further relates to the use of the pigments of the invention in polymers. Besides the additional protection afforded by the coating of the invention, the pigments can be readily incorporated and dispersed into the polymers, thermoplastic polymers for example.

Examples of thermoplastic polymers are polyoxyalkylenes, polycarbonates (PC), polyesters such as polybutylene terephthalate (PBT) or polyethylene terephthalate (PET), polyolefins such as polyethylene (PE) or polypropylene (PP), poly(meth)acrylates, polyamides, vinylaromatic (co) polymers such as polystyrene, impact-modified polystyrene such as HI-PS, or ASA, ABS or AES polymers, polyarylene ethers such as polyphenylene ethers (PPE), polysulfones, polyurethanes, polylactides, halogen-containing polymers, polymers containing imide groups, cellulose esters, silicone polymers, or thermoplastic elastomers. Mixtures of different thermoplastics may also be used.

In the case of further embodiments, the cosmetic is selected from the group consisting of body powder, face powder, pressed and loose powder, face makeup, cream powder, cream makeup, emulsion makeup, wax makeup, foundation, mousse makeup, rouge, eye makeup such as eyeshadow, mascara, eyeliner, liquid eyeliner, eyebrow pencil, lip care stick, lipstick, lip gloss, lip liner, hairstyling compositions such as hair spray, hair mousse, hair gel, hair wax, hair mascara, permanent or semipermanent hair colors, temporary hair colors, skincare compositions such as lotions, gels, emulsions, and nail varnish compositions.

The present invention further relates to the use of the inorganic/organic hybrid layer of the invention for producing protective layers on articles with a metallic surface, especially pigments.

The present invention relates, moreover, to the use of a precondensed heteropolysiloxane as specified above for the coating of metal oxide-containing surfaces.

According to an aspect 1, the present invention relates to a pigment comprising a metallic substrate and at least one inorganic/organic hybrid layer,
the inorganic/organic hybrid layer comprising at least one metal oxide, at least one network former, and at least one organic polymer,
the at least one metal oxide not constituting an oxidation product of the metallic substrate, and the term "metal oxide" embracing oxides, hydroxides, and oxide hydrates of the metals and semimetals,
the network former being joined at least partially covalently to the metal oxide and to the organic polymer, and
the ratio of the amount of metal oxide of the coating to the specific surface area of the uncoated metal pigment being in a range from 16.1 mg/m$^2$ to 25 mg/m$^2$, preferably in a range from 17.2 mg/m$^2$ to 23 mg/m$^2$, more preferably in a range from 17.9 mg/m$^2$ to 22.3 mg/m$^2$, and
the ratio of the amount of organic polymer of the inorganic/organic hybrid layer to the specific surface area of the uncoated metal pigment being in a range from 3.9 mg/m$^2$ to 10.1 mg/m$^2$, preferably in a range from 4.6 mg/m$^2$ to 9.7 mg/m$^2$, more preferably in a range from 5.1 mg/m$^2$ to 9.5 mg/m$^2$.

According to an aspect 2, the present invention relates to a pigment according to aspect 1, the metallic substrate being platelet-shaped.

According to an aspect 3, the present invention relates to a pigment according to one of aspects 1 and 2, the weight ratio of the amount of metal oxide of the coating to the amount of organic polymer of the inorganic/organic hybrid layer being in a range from 2.5:1 to 9.0:1, more preferably in a range from 3.0:1 to 8.1:1, more preferably still in a range from 3.3:1 to 6.7:1.

According to an aspect 4, the present invention relates to a pigment according to any of aspects 1 to 3, the ratio of the amounts of substance in moles of network former to organic polymer of the inorganic/organic hybrid layer being in the range from 1:10 to 5:10, more preferably in the range from 1.2:10 to 4:10, more preferably still in the range from 1.4:10 to 3.5:10.

According to an aspect 5, the present invention relates to a pigment according to any of aspects 1 to 4, the organic polymer not being polyethylene.

According to an aspect 6, the present invention relates to a pigment according to any of aspects 1 to 5, the thickness of the inorganic/organic hybrid layer being at least 40%, more preferably at least 60%, more preferably still at least 85% of the total thickness of the coating.

According to an aspect 7, the present invention relates to a pigment according to any of aspects 1 to 6, the amount of the inorganic/organic hybrid layer being at least 5 wt %, more preferably at least 6 wt %, more preferably still at least 8 wt %, based in each case on the total weight of the pigment.

According to an aspect 8, the present invention relates to a pigment according to any of aspects 1 to 7, the amount of the inorganic/organic hybrid layer being at most 25 wt %, more preferably at most 21 wt %, more preferably still at most 18 wt %, based on the total weight of the pigment.

According to an aspect 9, the present invention relates to a pigment according to any of aspects 1 to 8, the at least one metal oxide of the inorganic/organic hybrid layer being selected from the group consisting of silicon oxide, aluminum oxide, boron oxide, zirconium oxide, cerium oxide, iron oxide, titanium oxide, chromium oxide, tin oxide, molybdenum oxide, vanadium oxide, zinc oxide, magnesium oxide, and mixtures thereof, more preferably from the group consisting of silicon oxide, aluminum oxide, iron oxide, and mixtures thereof, more preferably still from silicon oxide, aluminum oxide, and mixtures thereof, the term metal oxide also embracing oxide hydrates and hydroxides.

According to an aspect 10, the present invention relates to a pigment according to any of aspects 1 to 9, at least one precondensed heteropolysiloxane having been applied to at least one inorganic/organic hybrid layer, the at least one precondensed heteropolysiloxane comprising at least one aminosilane and at least one silane selected from the group consisting of alkylsilanes, vinylsilanes, and arylsilanes, and the heteropolysiloxane having been applied in precondensed form.

According to an aspect 11, the present invention relates to a pigment according to any of aspects 1 to 10, the precondensed heteropolysiloxane being applied as an outermost layer to an enveloping inorganic/organic hybrid layer.

According to an aspect 12, the present invention relates to a pigment according to any of aspects 1 to 11, the amount of metal oxide in the coating being in a range from 50 wt % to 86 wt %, preferably in a range from 56 wt %, to 82 wt %, more preferably still in a range from 61 wt %, to 79 wt %, based in each case on the total weight of the coating.

According to an aspect 13, the present invention relates to a pigment according to any of aspects 1 to 12, at least 87 wt %, preferably at least 93 wt %, more preferably at least 97 wt % of the silane monomer components of the precondensed heteropolysiloxane being selected from the group consisting of aminosilanes, alkylsilanes, and mixtures thereof, based in each case on the total weight of the precondensed heteropolysiloxane.

According to an aspect 14, the present invention relates to a pigment according to any of aspects 1 to 13, the metal of the metallic substrate of the coated metal pigment according to any of aspects 1 to 25 consisting largely of a metal selected from the group consisting of aluminum, copper, iron, zinc, tin, titanium, chromium, cobalt, silver, stainless steel, nickel, antimony, magnesium, zirconium, silicon, boron, mixtures thereof, and alloys thereof.

According to an aspect 15, the present invention relates to a pigment according to any of aspects 1 to 14, the at least one aminosilane component of the precondensed heteropolysiloxane being selected to an extent of at least 92 wt %, based on the total weight of the aminosilane components present in the precondensed heteropolysiloxane, preferably completely, from the group consisting of $(H_2N(CH_2)_3)Si(OCH_3)_3$ ((3-aminopropyl)(trimethoxy)silane, AMMO), $(H_2N(CH_2)_3)Si(OC_2H_5)_3$ ((3-aminopropyl)(triethoxy)silane, AMEO), $(H_2N(CH_2)_2)NH(CH_2)_3)Si(OCH_3)_3$ ((N-(2-aminoethyl)-3-aminopropyl)(trimethoxy)silane, (DAMO)), (N-(2-aminoethyl)-3-aminopropyl)(triethoxy)silane, and mixtures thereof.

According to an aspect 16, the present invention relates to a pigment according to any of aspects 1 to 15, the at least one aminosilane of the precondensed heteropolysiloxane being selected from the group of the aminosilanes of formula (I):

$$R^{a1}_{x1}R^{b1}_{y1}R^{c1}_{(4-x1-y1)}Si \qquad (I),$$

the $R^{a1}$s independently of one another being selected from functional groups substituted by at least one nitrogen group, the functional group being selected from the group consisting of C1-C16 alkyl groups, C2-C8 alkenyl groups, C2-C8 alkynyl groups and phenyl groups, C7-C12 alkylaryl groups, and C7-C12 arylalkyl groups, the $R^{b1}$s independently of one another being selected from the group consisting of C1-C16 alkyl groups, C2-C8 alkenyl groups, C2-C8 alkynyl groups, phenyl groups, C7-C12 arylalkyl groups, and C7-C12 alkylaryl groups, the aforesaid groups being unsubstituted, the $R^{c1}$s independently of one another being selected from the group of the alkoxy groups,
x1 being 1, 2 or 3, and
y1 being selected from the group of the integers from 0 to (3−x1).

According to an aspect 17, the present invention relates to a pigment according to any of aspects 1 to 16, at least 95 wt % of the metal of the metallic substrate being selected from the group consisting of aluminum, iron, copper, and brass, based on the weight of the metal of the metallic substrate without oxygen.

According to an aspect 18, the present invention relates to a pigment according to any of aspects 1 to 17, the pigments having an aspect ratio $(D_{50}/h_{50})$ in a range from 1500:1 to 10:1, preferably from 1200:1 to 15:1, more preferably from 950:1 to 25:1.

According to an aspect 19, the present invention relates to a pigment according to any of aspects 1 to 18, at least one network former being selected from the compounds of formula (NI) or (NII),

$$R^{an1}_{xn1}R^{bn1}_{yn1}SiX_{(4-xn1-yn1)} \qquad (NI)$$

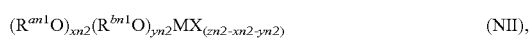

$$(R^{an1}O)_{xn2}(R^{bn1}O)_{yn2}MX_{(zn2-xn2-yn2)} \qquad (NII),$$

the Xs independently of one another being selected from hydrolyzable groups after whose hydrolysis a covalent bond of organic network former to the inorganic network can be formed,
the $R^{an1}$s independently of one another being selected from reactive organic groups which can be joined covalently to the organic polymer,
the $R^{bn1}$s independently of one another being selected from organic groups which can be joined covalently to the organic polymer,
M being selected from the group consisting of Al, Zr, and Ti,
xn1 being an integer from 1 to 3, yn1 being an integer from 0 to (3−xn1), zn2 being the formal oxidation number of M, xn2 being an integer from 1 to (zn2−1),
yn2 being an integer from 0 to (zn2−2), and
xn2+yn2≤zn2−1.

According to an aspect 20, the present invention relates to a pigment according to any of aspects 1 to 19, at least one network former being selected from the compounds of formula (NI) or (NII),

$$R^{an1}_{xn1}R^{bn1}_{yn1}SiX_{(4-xn1-yn1)} \qquad (NI)$$

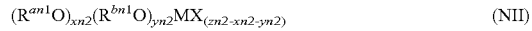

$$(R^{an1}O)_{xn2}(R^{bn1}O)_{yn2}MX_{(zn2-xn2-yn2)} \qquad (NII)$$

where the Xs independently of one another are selected from the group consisting of halogen groups, the hydroxyl group, and C1-C4 alkoxy groups without heteroatoms in the carbon chain,
the $R^{an1}$s independently of one another are selected from the group consisting of C1-C26 alkyl groups, C2-C26 alkenyl groups, C2-C26 alkynyl groups, C6-C30 aryl groups, C7-C31 alkylaryl groups, C7-C31 arylalkyl groups, C8-C32 alkenylaryl groups, C5-C20 cycloalkyl groups, C6-C21 alkylcycloalkyl groups, and C6-C21 cycloalkylalkyl groups, with any substituents present being selected from the group consisting of amino groups, hydroxyl group, thiol groups, epoxy groups, acrylate groups, methacrylate groups, vinyl groups, allyl groups, carboxyl groups, carboxylic anhydride groups, isocyanate groups, cyanate groups, ureido groups, carbamate groups, and mixtures thereof,
the $R^{bn1}$s independently of one another are selected from the group consisting of C1-C24 alkyl groups, C2-C24 alkenyl groups, C2-C24 alkynyl groups, C6-C24 aryl groups, fluorinated C6-C24 aryl groups, partially fluorinated C6-C24 aryl groups, C7-C30 alkylaryl groups, C7-C30 arylalkyl groups, C8-C30 alkenylaryl groups, C8-C30 arylalkenyl groups, C8-C30 arylalkynyl groups, C8-C30 alkynylaryl groups, C5-C20 cycloalkyl groups, and C6-C25 alkylcycloalkyl groups, more preferably still from the group consisting of C1-C24 alkyl groups, C2-C24 alkenyl groups, C6-C18 aryl groups, C7-C24 alkylaryl groups, C7-C24 arylalkyl groups, C5-C16 cycloalkyl groups, and C6-C20 alkylcycloalkyl groups, where the aforesaid groups are unsubstituted and any heteroatoms present in the carbon chains and carbon ring systems are selected from the group consisting of O, N, and S,
M being selected from the group consisting of Al, Zr, and Ti,
xn1 being an integer from 1 to 3, yn1 being an integer from 0 to (3−xn1),
zn2 being the formal oxidation number of M, xn2 being an integer from 1 to (zn2 1),
yn2 being an integer from 0 to (zn2−2), and
xn2+yn2≤zn2−1.

According to an aspect 21, the present invention relates to a pigment according to any of aspects 1 to 20, the inorganic/organic hybrid layer comprising at least one network former of formula (NI).

According to an aspect 22, the present invention relates to a pigment according to any of aspects 1 to 21, the organic polymer being selected from the group consisting of polyacrylates, polymethacrylates, polyethers, polyesters, polyamines, polyamides, polyols, polyurethanes, and polyolefins, the polyolefins including no polyethylene, more preferably from the group consisting of polyacrylates, polymethacrylates, polyethers, and polyesters, more preferably still from the group consisting of polyacrylates and polymethacrylates.

According to an aspect 23, the present invention relates to a method for producing metal pigments comprising metallic substrate and coating, comprising the following steps:
i) reacting at least one metal oxide reactant, at least one reactant of an organic polymer, and at least one network former in a liquid phase to form a coating composition, ii) applying the coating composition to metallic substrates to form an inorganic/organic hybrid layer,
the inorganic/organic hybrid layer comprising at least one inorganic network comprising at least one metal oxide and at least one organic polymer, and the inorganic network and the organic polymer being joined covalently to one another, the at least one metal oxide not constituting an oxidation product of the metallic substrate, and the term "metal oxide" embracing oxides, hydroxides, and oxide hydrates of the metals and semimetals,
the network former being joined at least partially to the metal oxide and to the organic polymer, and
the ratio of the amount of metal oxide of the coating to the specific surface area of the uncoated metal pigment being in a range from 16.1 mg/m$^2$ to 25 mg/m$^2$, preferably in a range from 17.2 mg/m$^2$ to 23 mg/m$^2$, more preferably in a range from 17.9 mg/m$^2$ to 22.3 mg/m$^2$, and
the ratio of the amount of organic polymer of the inorganic/organic hybrid layer to the specific surface area of the uncoated metal pigment being in a range from 3.9 mg/m$^2$ to 10.1 mg/m$^2$, preferably in a range from 4.6 mg/m$^2$ to 9.7 mg/m$^2$, more preferably in a range from 5.1 mg/m$^2$ to 9.5 mg/m$^2$.

According to an aspect 24, the present invention relates to a method for producing metal pigments with metallic substrate and coating according to aspect 23, the metallic substrate being platelet-shaped.

According to an aspect 25, the present invention relates to a method for producing metal pigments with metallic substrate and coating according to one of aspects 23 and 24, the weight ratio of the amount of metal oxide of the coating to the amount of organic polymer of the inorganic/organic hybrid layer of the coated metal pigments being in a range from 2.5:1 to 9.0:1, more preferably in a range from 3.0:1 to 8.1:1, more preferably still in a range from 3.3:1 to 6.7:1.

According to an aspect 26, the present invention relates to a method for producing metal pigments with metallic substrate and coating according to any of aspects 23 to 25, the ratio of the amounts of substance in moles of network former to organic polymer of the inorganic/organic hybrid layer of the coated metal pigments being in the range from 1:10 to 5:10, more preferably in the range from 1.2:10 to 4:10, more preferably still in the range from 1.4:10 to 3.5:10.

According to an aspect 27, the present invention relates to a method for producing metal pigments with metallic substrate and coating according to any of aspects 23 to 26, the amount of the inorganic/organic hybrid layer being at least 5 wt %, more preferably at least 6 wt %, more preferably still at least 8 wt %, based in each case on the total weight of the pigment.

According to an aspect 28, the present invention relates to a method for producing metal pigments with metallic substrate and coating according to any of aspects 23 to 27, the amount of metal oxide in the coating being in a range from 50 wt % to 86 wt %, preferably in a range from 56 wt %, to 82 wt %, more preferably in a range from 61 wt %, to 79 wt %, based in each case on the total weight of the coating.

According to an aspect 29, the present invention relates to a method for producing metal pigments with metallic substrate and coating according to any of aspects 23 to 28, at least one coating layer comprising at least one precondensed heteropolysiloxane being applied to at least one inorganic/organic hybrid layer, the term "metal oxide" also embracing oxide hydrates and hydroxides, and the at least one precondensed heteropolysiloxane comprising at least one aminosilane and at least one silane selected from the group of alkylsilanes, vinylsilanes, and arylsilanes.

According to an aspect 30, the present invention relates to a method for producing metal pigments with metallic substrate and coating according to any of aspects 23 to 29, the reaction of the reactants of the inorganic/organic hybrid layer being carried out either a) first at a pH of at most 6.8 and later at a pH of at least 7.2 or b) first at a pH of at least 7.2 and later at a pH of at most 6.8.

According to an aspect 31, the present invention relates to a method for producing metal pigments with metallic substrate and coating according to any of aspects 23 to 30, the reaction of the reactants of the inorganic/organic hybrid layer being carried out either a) first in a pH range from 2.5 to 6.8 and later in a pH range from 7.2 to 11.5, more preferably first in a pH range from 3.5 to 6.5 and later in a pH range from 7.5 to 11, more preferably still first in a pH range from 4 to 6 and later in a pH range from 8 to 10.2, or b) first in a pH range from 7.2 to 11.5 and later in a pH range from 2.5 to 6.8, more preferably first in a pH range from 7.5 to 11 and later in a pH range from 3.5 to 6.5, more preferably still first in a pH range from 8 to 10.2 and later in a pH range from 4 to 6.

According to an aspect 32, the present invention relates to a method for producing metal pigments with metallic substrate and coating according to any of aspects 23 to 31, the reaction of the reactants of the inorganic/organic hybrid layer being carried out first at a pH of at most 6.8, more preferably first at a pH of at most 6.5, more preferably still first at a pH of at most 6.

According to an aspect 33, the present invention relates to a pigment produced by means of a method according to any of aspects 23 to 32.

According to an aspect 34, the present invention relates to the use of the pigments according to any of aspects 1 to 22 in a cosmetic, a plastic or a coating material.

According to an aspect 35, the present invention relates to the use according to aspect 34, the coating material being selected from the group consisting of wet paints and varnishes, powder coatings and inks such as printing inks and liquid inks.

According to an aspect 36, the present invention relates to a coating material comprising a pigment according to any of aspects 1 to 22.

According to an aspect 37, the present invention relates to an article, the article comprising pigments according to any of aspects 1 to 22 or a coating material according to aspect 36.

EXAMPLES

Example 1

100 g of aluminum pigment in the form of a powder or in the form of a paste are admixed with isopropanol until there is 250 g of suspension in each case. The suspension is heated to 70° C., after which the constituents of the inorganic/organic hybrid layer (tetraethyl orthosilicate (TEOS), Dynasylan MEMO, TMPTMA, azobis(isobutyronitrile) (AIBN) and, if desired, allyl methacrylate or lauryl methacrylate) and 3 g of acetic acid in 30 g of distilled water are added. After 3 hours, 2.5 g of ethylenediamine in 50 g of isopropanol are added. After a further 2 hours, Dynasylan OCTEO and Dynasylan DAMO are added and the reaction mixture is stirred for 1 h before being cooled. The solid is isolated by filtration and collected as a paste.

|  | Pigment | BET [m²/g] | Amount of pigment [g] | TEOS [g] | MEMO [g] | TMPTMA [g] | Lauryl methacrylate [g] | Allyl methacrylate [g] | AIBN [g] | OCTEO [g] | DAMO [g] |
|---|---|---|---|---|---|---|---|---|---|---|---|
| B 1-1 | Mex 2192 | 4.0 | 100.00 | 35.0 | 0.4 | 1.8 | 0.4 | 0.0 | 0.1 | 0.9 | 1.0 |
| B 1-2 | Mex 3580 | 6.1 | 100.00 | 45.0 | 0.6 | 2.4 | 0.5 | 0.0 | 0.2 | 1.3 | 1.6 |
| B 1-3 | Mex 3580 | 6.1 | 100.00 | 40.1 | 0.8 | 3.6 | 0.7 | 0.0 | 0.3 | 1.3 | 0.7 |
| B 1-4 | Metallic 707 | 5.8 | 100.00 | 46.4 | 0.6 | 2.6 | 0.5 | 0.0 | 0.2 | 1.4 | 1.9 |
| B 1-5 | Mex 3580 | 6.1 | 100.00 | 42.1 | 0.5 | 2.2 | 0.8 | 0.0 | 0.2 | 1.3 | 1.6 |
| B 1-6 | Mex 3540 | 2.6 | 100.00 | 23.5 | 0.3 | 1.2 | 0.2 | 0.0 | 0.1 | 0.6 | 0.7 |
| B 1-7 | Mex 9160 | 6.5 | 100.00 | 52.4 | 0.7 | 3.1 | 0.6 | 0.0 | 0.3 | 1.4 | 1.6 |
| B 1-8 | Mex 3580 | 6.1 | 100.00 | 42.2 | 0.5 | 2.2 | 0.4 | 0.0 | 0.2 | 2.5 | 1.1 |
| VB 1-9 | Mex 3580 | 6.1 | 100.00 | 42.2 | 0.0 | 2.2 | 0.4 | 0.0 | 0.2 | 2.5 | 1.1 |
| B 1-10 | Mex 2192 | 4.0 | 100.00 | 45.0 | 0.5 | 2.1 | 0.0 | 0.0 | 0.2 | 1.3 | 1.2 |
| B 1-11 | Mex 3580 | 6.1 | 100.00 | 41.2 | 0.7 | 2.7 | 0.0 | 0.0 | 0.2 | 1.5 | 1.0 |
| B 1-12 | Mex 3540 | 2.6 | 100.00 | 44.1 | 0.7 | 2.6 | 0.0 | 0.0 | 0.1 | 1.0 | 0.9 |
| B 1-13 | Mex 9160 | 6.5 | 100.00 | 35.7 | 0.6 | 3.0 | 0.0 | 0.0 | 0.3 | 0.9 | 1.3 |
| B 1-14 | Mex 2192 | 4.0 | 100.00 | 42.5 | 0.5 | 2.9 | 0.0 | 0.6 | 0.1 | 1.2 | 1.5 |
| B 1-15 | Mex 3580 | 6.1 | 100.00 | 44.2 | 0.4 | 3.1 | 0.0 | 0.7 | 0.2 | 1.2 | 1.7 |
| B 1-16 | Mex 3540 | 2.6 | 100.00 | 41.7 | 0.7 | 2.2 | 0.0 | 0.5 | 0.2 | 1.5 | 1.2 |

B: Inventive example,
VB: Comparative example

Example 2

Inventive example 2-1 took place in analogy to the protocol of example 1. Comparative example 2-2 took place in accordance with the following protocol: 100 g of aluminum pigment in the form of a powder or in the form of a paste are admixed with isopropanol until there are 250 g of suspension in each case. The suspension is heated to 70° C., after which the tetraethyl orthosilicate (TEOS) and 3 g of acetic acid in 30 g of distilled water are added. After 3 hours, the additions of MEMO, TMPTMA, lauryl methacrylate, and AIBN take place. After a further 3 hours, 2.5 g of ethylenediamine in 50 g of isopropanol are added. After another 2 hours, Dynasylan OCTEO and Dynasylan DAMO are added, and the reaction mixture is stirred for 1 h before being cooled. The solid is isolated by filtration and collected as a paste.

|  | Pigment | BET [m²/g] | Amount of pigment [g] | TEOS [g] | MEMO [g] | TMPTMA [g] | Lauryl methacrylate [g] | AIBN [g] | OCTEO [g] | DAMO [g] |
|---|---|---|---|---|---|---|---|---|---|---|
| B 2-1 | Mex 2156 | 3.4 | 200.00 | 45.9 | 0.6 | 2.4 | 0.5 | 0.2 | 1.0 | 1.3 |
| VB 2-2 | Mex 2156 | 3.4 | 200.00 | 45.9 | 0.6 | 2.4 | 0.5 | 0.2 | 1.0 | 1.3 |

B: Inventive example,
VB: Comparative example

Example 3

100 g of aluminum pigment in the form of a powder or in the form of a paste are admixed with isopropanol until there are 250 g of suspension in each case. The suspension is heated to 70° C., after which the constituents of the inorganic/organic hybrid layer and 3 g of acetic acid in 30 g of distilled water are added. After 3 hours, 2.5 g of ethylenediamine in 50 g of isopropanol are added. After a further 2 hours, Dynasylan OCTEO and Dynasylan DAMO are added and the reaction mixture is stirred for 1 h before being cooled. The solid is isolated by filtration and collected as a paste.

|  | Pigment | BET [m²/g] | Amount of pigment [g] | TEOS [g] | MEMO [g] | TMPTMA [g] | Lauryl methacrylate [g] | AIBN [g] | OCTEO [g] | DAMO [g] |
|---|---|---|---|---|---|---|---|---|---|---|
| VB 3-1 | Mex 2153 | 1.7 | 100.0 | 19.3 | 0.2 | 0.9 | 0.2 | 0.1 | 0.2 | 0.3 |
| VB 3-2 | Mex 2156 | 3.4 | 100.0 | 20.7 | 0.5 | 2.2 | 0.4 | 0.2 | 0.7 | 0.9 |
| B 3-3 | Mex 2156 | 3.4 | 100.0 | 23.1 | 0.6 | 2.7 | 0.5 | 0.2 | 1.0 | 0.4 |
| B 3-4 | Mex 3580 | 6.1 | 100.0 | 50.7 | 0.6 | 2.7 | 0.5 | 0.2 | 1.3 | 1.6 |
| VB 3-5 | Mex 3580 | 6.1 | 100.0 | 32.2 | 0.5 | 2.2 | 0.4 | 0.2 | 1.3 | 1.6 |
| B 3-6 | Mex 3580 | 6.1 | 100.0 | 42.2 | 0.5 | 2.2 | 0.4 | 0.2 | 1.3 | 0.7 |
| B 3-7 | Mex 2192 | 4.0 | 100.0 | 35.0 | 0.4 | 1.8 | 0.4 | 0.1 | 0.5 | 0.5 |
| B 3-8 | Metallic 707 | 5.8 | 100.0 | 38.0 | 1.0 | 4.3 | 0.8 | 0.3 | 1.5 | 0.6 |
| VB 3-9 | Metallux 9157 | 5.2 | 100.0 | 41.1 | 1.1 | 4.6 | 0.9 | 0.4 | 1.6 | 0.6 |

-continued

|  | Pigment | BET [m²/g] | Amount of pigment [g] | TEOS [g] | MEMO [g] | TMPTMA [g] | Lauryl meth-acrylate [g] | AIBN [g] | OCTEO [g] | DAMO [g] |
|---|---|---|---|---|---|---|---|---|---|---|
| B 3-10 | Metallux 9157 | 5.2 | 100.0 | 39.3 | 0.6 | 2.3 | 0.5 | 0.2 | 0.7 | 0.8 |
| VB 3-11 | Mex 2156 | 3.4 | 100.0 | 23.1 | 0.6 | 2.7 | 0.5 | 0.2 | 1.0 | 0.4 |
| B 3-12 | Mex 3580 | 6.1 | 100.0 | 53.9 | 0.5 | 2.2 | 0.4 | 0.2 | 1.3 | 0.5 |
| B 3-13 | Metallic 707 | 5.8 | 100.0 | 50.2 | 0.7 | 2.8 | 0.5 | 0.2 | 1.4 | 1.8 |
| B 3-14 | Metallux 9157 | 5.2 | 100.0 | 50.2 | 0.6 | 2.6 | 0.5 | 0.2 | 0.7 | 0.8 |
| VB 3-15 | Mex 2192 | 4.0 | 100.0 | 39.4 | 0.5 | 2.0 | 0.4 | 0.2 | 0.9 | 1.0 |

B: Inventive example,
VB: Comparative example

Application Example 1

For a stringent gassing test, 15 g of metal pigment paste with a solids content of 55 wt % were suspended in 11.0 g of butyl glycol with a stirring time of 5 minutes. This suspension was admixed with 14.4 g of colorless binder (ZK26-6826-402, manufacturer: BASF Coatings) and 0.6 g of 10% strength dimethylethanolamine solution (solvent: water) and stirred for 5 minutes.

21.96 g of the suspension were incorporated with stirring into a mixture of 195.0 g of mixing varnish for effect substance testing, milky/colorless (ZW42-6008-0101, manufacturer: BASF Coatings), 75.6 g of red aqueous basecoat tinting paste (ZU560-329-0001, manufacturer: BASF Coatings, containing red iron oxide, $Fe_2O_3$) and 6.0 g of black aqueous basecoat tinting paste (ZU42-5943-0001, manufacturer: BASF Coatings, containing black iron oxide, $Fe_2O_3*FeO$). Thereafter the pH of the suspension was adjusted to 9.0 using 10% strength dimethylethanolamine solution (solvent water).

265 g of the above composition were introduced into a gassing flask which was sealed with a twin-chamber gas bubble counter. The gas wash bottle was conditioned in a water bath at 40° C. for 1 hour, given a gastight seal, and tested over a maximum of 41 days. The resulting gas volume was read off on the basis of the displaced water volume in the upper chamber of the gas bubble counter. On evolution of at most 10 ml of hydrogen after 41 days, the test was deemed to have been passed. If the sample was not stable over the entire period, the time until outgassing of the sample was recorded.

| | Metal oxide to surface area [mg/m²] | Organic polymer to surface area [mg/m²] | Result |
|---|---|---|---|
| B 1-1 | 22.6 | 5.3 | passed |
| B 1-2 | 20.3 | 5.0 | passed |
| B 1-3 | 17.9 | 7.1 | passed |
| B 1-4 | 20.7 | 5.1 | passed |
| B 1-5 | 17.7 | 4.8 | passed |
| B 1-6 | 23.0 | 5.5 | passed |
| B1-7 | 21.1 | 5.6 | passed |
| B 1-8 | 17.7 | 4.2 | passed |
| VB 1-9 | 17.6 | 3.9 | 2 days |
| B 2-1 | 17.5 | 4.2 | passed |
| VB 2-2 | 17.5 | 4.2 | 14 days |
| VB 3-1 | 26.8 | 5.4 | 6 |
| VB 3-2 | 12.8 | 6.2 | 2 |
| B 3-4 | 20.2 | 4.8 | passed |
| VB 3-5 | 13.9 | 4.3 | 20 |
| B 3-6 | 18.0 | 4.3 | passed |
| B 3-7 | 22.9 | 5.4 | passed |
| B 3-8 | 17.3 | 8.7 | passed |
| B 3-10 | 20.5 | 5.4 | passed |
| B 3-12 | 24.1 | 4.5 | passed |
| B 3-13 | 22.5 | 5.7 | passed |

B: Inventive example,
VB: Comparative example

Application Example 2

The pigment samples were incorporated into a typical test varnish system (ZW42-1100, BASF, 0.35 wt % metal fraction) and the test applications were produced by spray coating on a primed steel panel. The film thickness in this case was 6 μm. The basecoat was coated over with a commercial 1K clearcoat, followed by baking. The measurements were carried out using a BYK mac instrument (from Byk-Gardner).

The flop index according to Alman is defined as follows in the relevant literature:

$$\text{Flop index} = 2.69 \cdot (L_{E1} - L_{E3})^{1.11} / L_{E2}^{0.86}$$

where $L_{E1}$ is the luminance of the near-to-specular measuring angle (E1=15° to the specular angle), $L_{E2}$ is the luminance of the measuring angle between near-to-specular and far-from-specular angle (E2=45° to the specular angle), and $L_{E3}$ is the luminance of the far-from-specular measuring angle (E3=110° to the specular angle). The changes in flop between the respective inventive example and the corresponding comparative examples are listed below.

The gloss measurement took place in a method based on DIN EN ISO 2813.

The lower the numerical value of the flop index, the more weakly the desired light/dark flop is manifested.

| | Metal oxide to surface area [mg/m²] | Organic polymer to surface area [mg/m²] | ΔFlop |
|---|---|---|---|
| VB 3-11 | 20.4 | 10.5 | −1.4 |
| B3-53 | 19.7 | 10.1 | 0 |

B: Inventive example,
VB: Comparative example

| | Metal oxide to surface area [mg/m²] | Organic polymer to surface area [mg/m²] | ΔFlop |
|---|---|---|---|
| B 3-7 | 22.9 | 5.4 | 0 |
| VB 3-15 | 37.6 | 5.6 | −0.7 |

B: Inventive example,
VB: Comparative example

| | Metal oxide to surface area [mg/m²] | Organic polymer to surface area [mg/m²] | ΔFlop |
|---|---|---|---|
| VB 3-9 | 22.5 | 11.3 | −0.7 |
| B3-10 | 20.5 | 5.4 | 0 |
| VB 3-14 | 25.6 | 6.1 | −0.3 |

B: Inventive example,
VB: Comparative example

The invention claimed is:

1. A pigment comprising a metallic substrate and at least one inorganic/organic hybrid layer,
wherein the inorganic/organic hybrid layer comprises at least one metal oxide, at least one network former, and at least one organic polymer,
wherein the at least one metal oxide does not constitute an oxidation product of the metallic substrate, and the term "metal oxide" comprises oxides, hydroxides, and oxide hydrates of the metals and semimetals,
wherein the network former is joined at least partially covalently to the metal oxide and to the organic polymer,
wherein the ratio of the amount of metal oxide of the inorganic/organic hybrid layer to the specific surface area of the uncoated metal pigment is in a range from 16.1 mg/m² to 25 mg/m², and
the ratio of the amount of organic polymer of the inorganic/organic hybrid layer to the specific surface area of the uncoated metal pigment is in a range from 3.9 mg/m² to 10.1 mg/m².

2. The pigment according to claim 1, wherein the metallic substrate is platelet-shaped.

3. The pigment according to claim 1, wherein the organic polymer is not polyethylene.

4. The pigment according to claim 1, wherein the ratio of the amount of metal oxide of the coating to the specific surface area of the uncoated metal pigment is in a range from 17.2 mg/m² to 23 mg/m².

5. The pigment according to claim 1, wherein the ratio of the amount of organic polymer of the inorganic/organic hybrid layer to the specific surface area of the uncoated metal pigment is in a range from 4.6 mg/m² to 9.7 mg/m².

6. The pigment according to claim 1, wherein the thickness of the inorganic/organic hybrid layer is at least 40% of the total thickness of the coating.

7. The pigment according to claim 1, wherein the amount of the inorganic/organic hybrid layer is at least 5 wt %, based on the total weight of the pigment.

8. The pigment according to claim 1, wherein the at least one metal oxide of the inorganic/organic hybrid layer is selected from the group consisting of silicon oxide, aluminum oxide, boron oxide, zirconium oxide, cerium oxide, iron oxide, titanium oxide, chromium oxide, tin oxide, molybdenum oxide, vanadium oxide, zinc oxide, magnesium oxide, and mixtures thereof, the term "metal oxide" also comprises oxide hydrates and hydroxides.

9. The pigment according to claim 1, wherein at least one heteropolysiloxane has been applied to at least one inorganic/organic hybrid layer,
wherein the at least one heteropolysiloxane is prepared from at least one aminosilane and at least one silane selected from the group consisting of alkylsilanes, vinylsilanes, and arylsilanes.

10. The pigment according to claim 1, wherein at least 95 wt % of the metal of the metallic substrate are selected from the group consisting of aluminum, iron, copper, and brass, based on the weight of the metal of the metallic substrate without oxygen.

11. The pigment according to claim 1, wherein at least one network former is selected from the compounds of formula (NI),

$$R^{an1}_{xn1}R^{bn1}_{yn1}SiX_{(4-xn1-yn1)} \qquad (NI)$$

wherein the Xs independently of one another are selected from hydrolyzable groups after whose hydrolysis a covalent bond of organic network former to the inorganic network can be formed,
the $R^{an1}$s independently of one another are selected from reactive organic groups which can be joined covalently to the organic polymer,
the $R^{bn1}$s independently of one another are selected from organic groups which can be joined covalently to the organic polymer,
xn1 is an integer from 1 to 3, and yn1 is an integer from 0 to (3−xn1).

12. The pigment according to claim 1, wherein the inorganic/organic hybrid layer comprises at least one network former of formula (NI),
wherein the Xs independently of one another are selected from the group consisting of C1-C4 alkoxy groups without heteroatoms in the carbon chain,
the $R^{an1}$s independently of one another are selected from the group consisting of substituted C1-C10 alkyl groups, the substituents are selected from the group consisting of acrylate groups, methacrylate groups and mixtures thereof,
the $R^{bn1}$s independently of one another are selected from the group consisting of C1-C24 alkyl groups, C6-C18 aryl groups, C7-C24 alkylaryl groups, C7-C24 arylalkyl groups, C5-C16 cycloalkyl groups, and C6-C20 alkylcycloalkyl groups, the aforesaid groups are unsubstituted and contain no heteroatoms in the carbon chains and carbon ring systems,
xn1 is an integer from 1 to 3, and
yn1 is an integer 0 or 1.

13. The pigment according to claim 1, wherein the organic polymer is selected from the group consisting of polyacrylates, polymethacrylates, polyethers, polyesters, polyamines, polyamides, polyols, polyurethanes, and polyolefins, the polyolefins including no polyethylene.

14. A method for producing metal pigments comprising metallic substrate and coating, comprising the following steps:
i) reacting at least one metal oxide reactant, at least one reactant of an organic polymer, and at least one network former in a liquid phase to form a coating composition,
ii) applying the coating composition to metallic substrates to form an inorganic/organic hybrid layer,
wherein the inorganic/organic hybrid layer comprises at least one inorganic network comprising at least one metal oxide and at least one organic polymer, and the inorganic network and the organic polymer are joined covalently to one another, the at least one metal oxide does not constitute an oxidation product of the metallic substrate, and the term "metal oxide" comprises oxides, hydroxides, and oxide hydrates of the metals and semimetals, the network former is joined at least partially to the metal oxide and to the organic polymer, the ratio of the amount of metal oxide of the inorganic/organic hybrid layer to the specific surface area of the uncoated metal pigment is in a range from 16.1 mg/m$^2$ to 25 mg/m$^2$, and the ratio of the amount of organic polymer of the inorganic/organic hybrid layer to the specific surface area of the uncoated metal pigment is in a range from 3.9 mg/m$^2$ to 10.1 mg/m$^2$.

15. The method according to claim 14, wherein at least one coating layer comprising at least one heteropolysiloxane is applied to at least one inorganic/organic hybrid layer, wherein the term "metal oxide" also comprises oxide hydrates and hydroxides, and the at least one heteropolysiloxane is prepared from at least one aminosilane and at least one silane selected from the group of alkylsilanes, vinylsilanes, and arylsilanes.

16. The method according to claim 14, wherein the reaction of the reactants of the inorganic/organic hybrid layer is carried out either a) first in a pH range from 2.5 to 6.8 and later in a pH range from 7.2 to 11.5, or b) first in a pH range from 7.2 to 11.5 and later in a pH range from 2.5 to 6.8.

17. An article comprising the pigment of claim 1, wherein the article is a cosmetic, a plastic or a coating material.

18. The pigment according to claim 9, wherein the at least one aminosilane of the heteropolysiloxane is selected from the group of the aminosilanes of formula (I):

$$R^{a1}_{x1}R^{b1}_{y1}R^{c1}_{(4-x1-y1)}Si \qquad (I),$$

the $R^{a1}$s independently of one another being selected from functional groups substituted by at least one nitrogen group, the functional group being selected from the group consisting of C1-C16 alkyl groups, C2-C8 alkenyl groups, C2-C8 alkynyl groups and phenyl groups, C7-C12 alkylaryl groups, and C7-C12 arylalkyl groups, the $R^{b1}$s independently of one another being selected from the group consisting of C1-C16 alkyl groups, C2-C8 alkenyl groups, C2-C8 alkynyl groups, phenyl groups, C7-C12 arylalkyl groups, and C7-C12 alkylaryl groups, the aforesaid groups being unsubstituted, the $R^{c1}$s independently of one another being selected from the group of the alkoxy groups, x1 being 1, 2 or 3, and y1 being selected from the group of the integers from 0 to (3−x1).

19. The method according to claim 14, wherein the weight ratio of the amount of metal oxide of the coating to the amount of organic polymer of the inorganic/organic hybrid layer of the coated metal pigments is in a range from 2.5:1 to 9.0:1.

20. The method according to claim 14, wherein the ratio of the amounts of substance in moles of network former to organic polymer of the inorganic/organic hybrid layer of the coated metal pigments is in the range from 1:10 to 5:10.

21. The pigment according to claim 9, wherein the at least one heteropolysiloxane has been applied to the at least one inorganic/organic hybrid layer in precondensed form.

* * * * *

UNITED STATES PATENT AND TRADEMARK OFFICE
CERTIFICATE OF CORRECTION

PATENT NO. : 10,557,037 B2
APPLICATION NO. : 15/546865
DATED : February 11, 2020
INVENTOR(S) : Simone Kreppner et al.

Page 1 of 1

It is certified that error appears in the above-identified patent and that said Letters Patent is hereby corrected as shown below:

In the Claims

Column 48, Line 17, Claim 11, after "(NI)" insert -- , --

Signed and Sealed this
Twelfth Day of May, 2020

Andrei Iancu
*Director of the United States Patent and Trademark Office*